(12) United States Patent
Wanders

(10) Patent No.: US 9,937,034 B2
(45) Date of Patent: Apr. 10, 2018

(54) INTRAOCULAR LENS ASSEMBLY

(71) Applicant: OCULENTIS HOLDING B.V., Eerbeek (NL)

(72) Inventor: Bernardus Franciscus Maria Wanders, Angerlo (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 0 days.

(21) Appl. No.: 14/913,310

(22) PCT Filed: Jul. 31, 2014

(86) PCT No.: PCT/NL2014/050537
§ 371 (c)(1),
(2) Date: Feb. 19, 2016

(87) PCT Pub. No.: WO2015/026226
PCT Pub. Date: Feb. 26, 2015

(65) Prior Publication Data
US 2016/0199176 A1    Jul. 14, 2016

(30) Foreign Application Priority Data

Aug. 20, 2013 (NL) .................................. 2011325
Oct. 4, 2013 (NL) .................................. 2011563
Apr. 18, 2014 (NL) .................................. 2012659

(51) Int. Cl.
A61F 2/16 (2006.01)

(52) U.S. Cl.
CPC ...... *A61F 2/1648* (2013.01); *A61F 2002/169* (2015.04); *A61F 2002/1681* (2013.01); *A61F 2002/1689* (2013.01); *A61F 2002/16902* (2015.04)

(58) Field of Classification Search
CPC .. A61F 2/16; A61F 2/1648; A61F 2002/1689; A61F 2002/169; A61F 2002/16902
USPC .................................................. 623/6.34, 6.38
See application file for complete search history.

(56) References Cited

U.S. PATENT DOCUMENTS

| | | | |
|---|---|---|---|
| 5,697,973 A | 12/1997 | Peyman et al. | |
| 7,806,929 B2 * | 10/2010 | Brown .................. | A61F 2/1602 623/6.39 |
| 2006/0047339 A1 | 3/2006 | Brown | |
| 2010/0016964 A1 * | 1/2010 | Werblin ................ | A61F 2/1648 623/6.34 |
| 2011/0251686 A1 * | 10/2011 | Masket ................. | A61F 2/1613 623/6.43 |
| 2013/0190868 A1 | 7/2013 | Kahook | |

FOREIGN PATENT DOCUMENTS

EP    2422746 A1    2/2012

* cited by examiner

*Primary Examiner* — David H Willse
*Assistant Examiner* — Javier Blanco
(74) *Attorney, Agent, or Firm* — AEON Law, PLLC; Adam L. K. Philipp; Jonathan E. Olson

(57) ABSTRACT

The invention provides an intra ocular lens assembly comprising an intra ocular lens structure (IOL) for placement in the capsular bag and securing the IOL in an opening in an anterior part of a capsular bag, with an anterior capsular bag flap surrounding said opening, and a secondary intraocular lens (S-IOL) comprising fixing parts for attaching said S-IOL to said IOL.

9 Claims, 26 Drawing Sheets

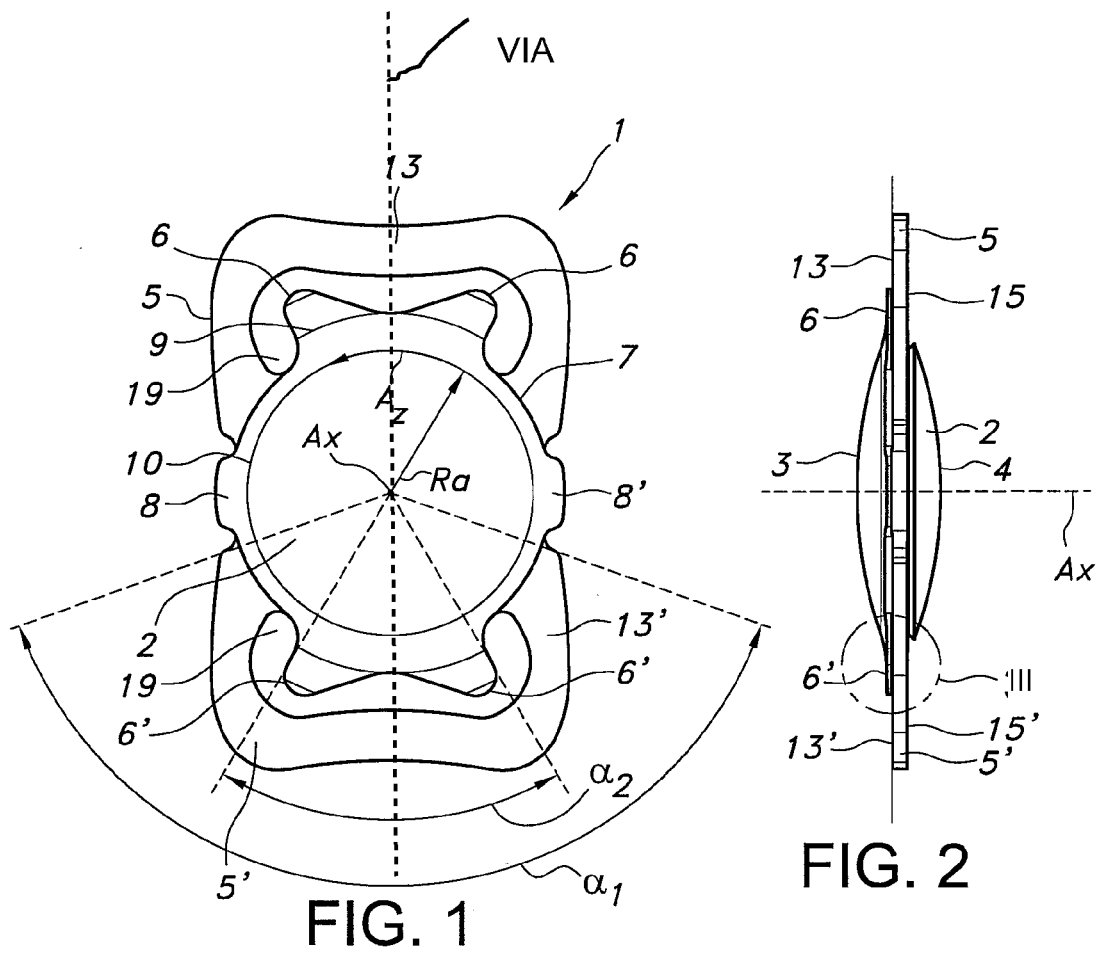
FIG. 1
FIG. 2
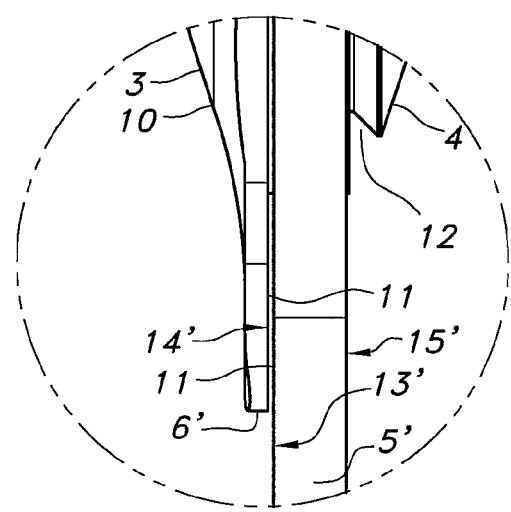
FIG. 3

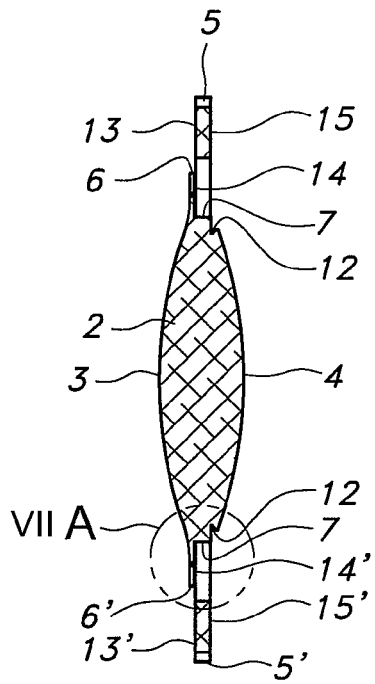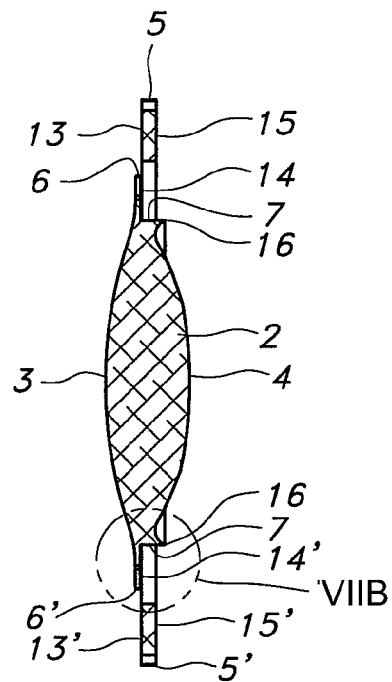
FIG. 6A     FIG. 6B
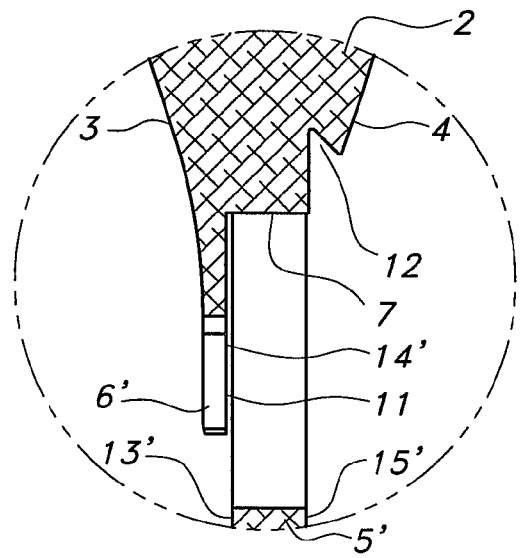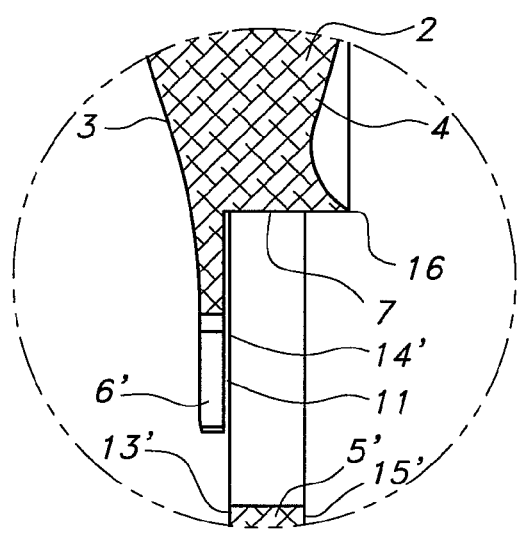
FIG. 7A     FIG. 7B

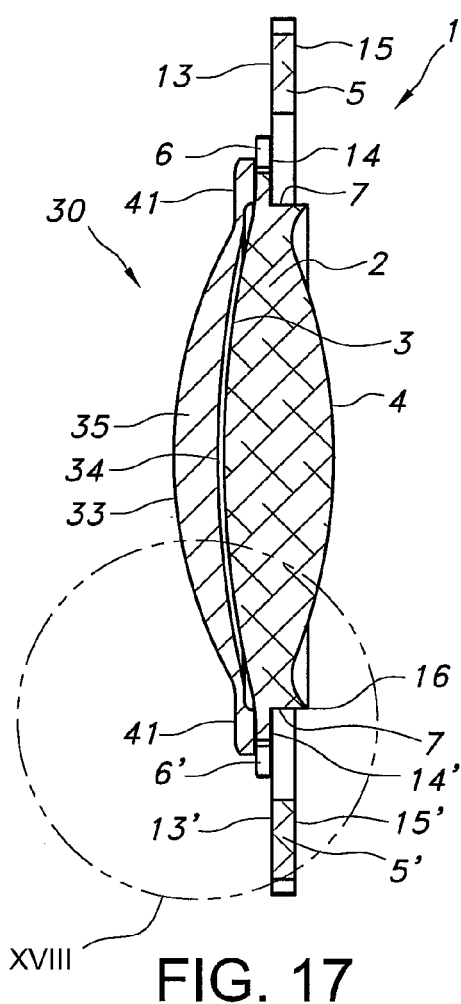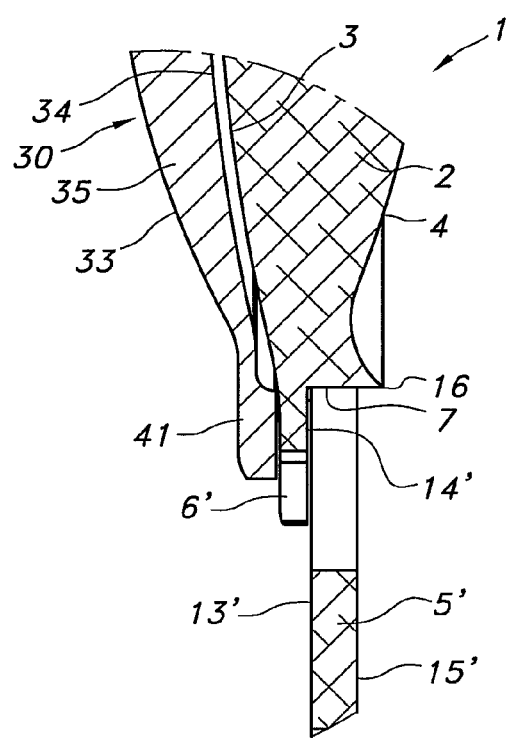
FIG. 17
FIG. 18

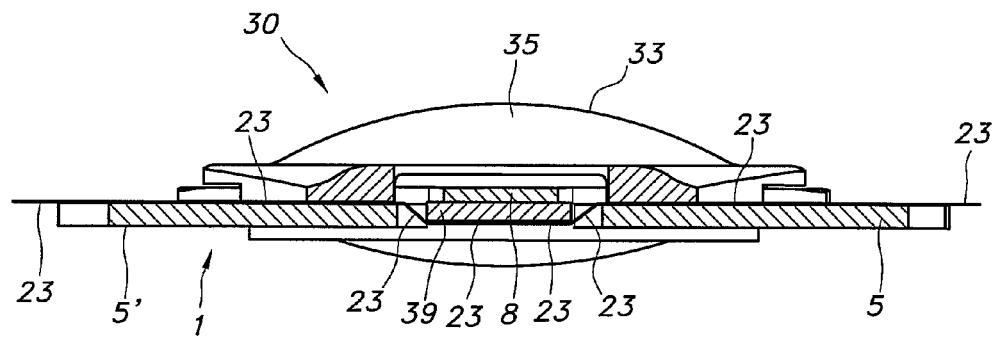
FIG. 27
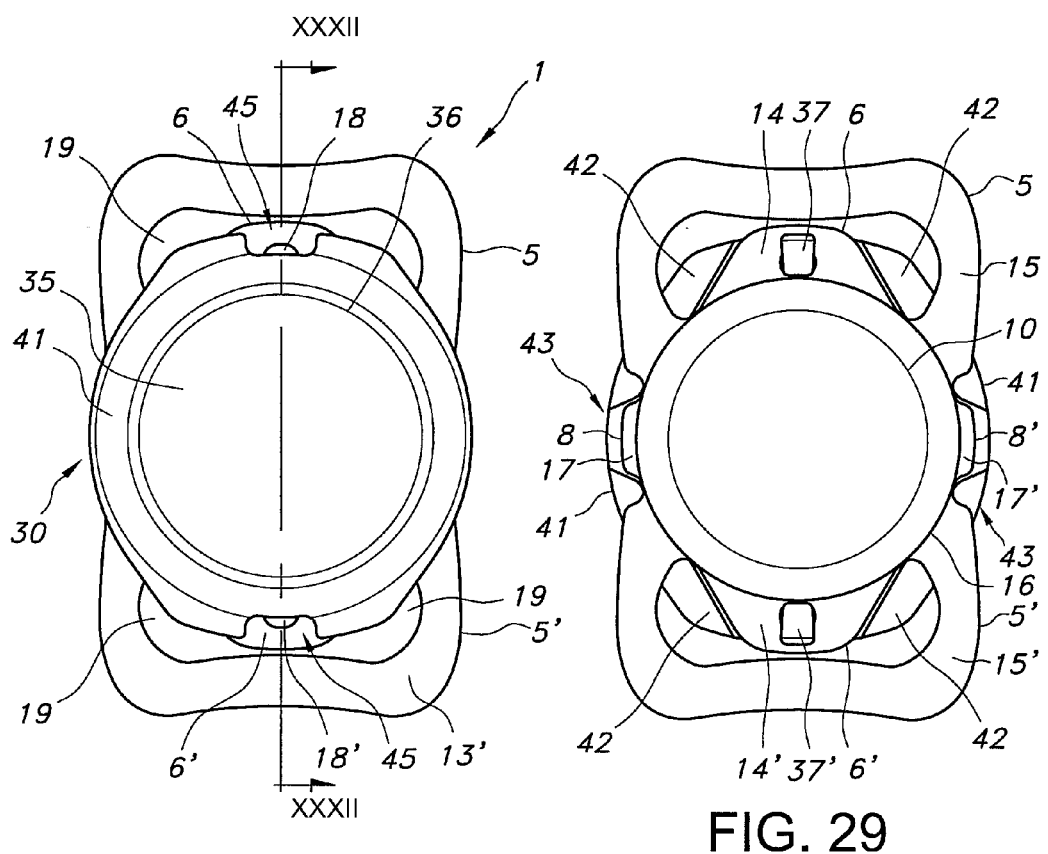
FIG. 28
FIG. 29

INTRAOCULAR LENS ASSEMBLY

FIELD OF THE INVENTION

The invention relates to an intraocular lens assembly comprising an intraocular lens structure (IOL) and a secondary intraocular lens, and a method for inserting such an intraocular lens assembly.

BACKGROUND OF THE INVENTION

In modern cataract procedures, also called extracapsular cataract extraction, a hole is cut in the anterior capsular bag. This may be done using laser devices. Subsequently, the natural lens is removed. In the remaining parts of the capsular bag, in many suggested procedures an IOL is placed. The IOL more or less maintains its position in the empty bag.

Usually, an IOL is provided with haptics. These haptics extend radially from a lens of an IOL. After implanting an IOL, these haptics usually engage the inside circumference of the remaining capsular bag part in order to more or less keep the optics, for instance a lens, of the IOL centred and positioned in the capsular bag.

For improving fixation of the position of an IOL, many designs were proposed. U.S. Pat. No. 6,027,531 describes in its abstract "An intraocular lens for use in extracapsular cataract extraction has a haptic pa[r]t that surrounds the optical pa[r]t of the lens and further contains a groove of such shape to accommodate the anterior and posterior capsules of the lens bag after anterior capsulorhexis, extracapsular cataract extraction and posterior capsulorhexis. The lens is preferably inserted in a calibrated, circular and continuous combined anterior and posterior capsulorhexis, slightly smaller than the inner circumference of the groove as to induce a stretching of the rims of the capsular openings. This new approach is believed to prevent the appearance of secondary opacification of the capsules, allows a very stable fixation of the intraocular lens and ensures a tight separation between the anterior and posterior segment of the eye. This new principle of insertion is called the bag-in-the-lens technique, in contrast with the classical lens in-the-bag technique.". Placement of this IOL requires skills and the capsular bag may get damaged. If after insertion the capsular bag ruptures, the IOL will not maintain its position.

In U.S. Pat. No. 6,881,225, in the abstract an intraocular lens structure for reducing complications is described. The intraocular lens structure comprises an optic, a support and a closing fixture. The closing fixture is a groove or a valley formed on the side portion of the optic of the intraocular lens. The valley is formed by the optic and a protrusion projecting posteriorly from the optic. The groove or the valley in the optic is made engaged with the posterior capsular opening generally over the entire circumference of the groove or the valley to close the opening of the posterior capsule. Like most of the current IOL structures, the structure also uses its haptics for keeping the structure in the capsular bag. The groove holds the posterior part of the capsular bag.

U.S. Pat. No. 5,171,320 in its abstract describes an intraocular lens system adapted to be implanted within a generally circular opening in an anterior wall of the capsular bag which normally contains the crystalline lens of an eye. The intraocular lens system includes a lens body having an annular groove which is formed in a peripheral portion thereof in a plane substantially perpendicular to an optical axis of the lens body. The lens body includes an optically effective portion located radially inside the annular groove, and an anterior lens portion and a posterior lens portion located on respective anterior and posterior sides of the annular groove. The intraocular lens system is secured in position within the circular opening such that an annular flap portion of the capsular bag which surrounds the circular opening is accommodated within the annular grove in the lens body.

Known IOL's and IOL systems usually do not completely correct optical errors in the eye. Usually, emmetropy, in which light is exactly focused on the retina, is not attained. A residual error remains. Often, the patient still needs spectacles, or receives laser treatment in order to correct the usual +0.5 to +1.5 Dioptre refractive error that remains. In the art, an additional lens was suggested that clips on an implanted IOL. Examples of these are the following documents.

U.S. Pat. No. 4,932,971 in its abstract describes a clip-on optic assembly for clipping in situ onto a previously implanted intraocular lens to change its optical characteristics without removal from the eye, comprising a lens body having a plurality of spaced apart resilient clip members extending therefrom and outwardly terminating in clips for gripping the implanted lens peripheral edge to clip the assembly thereon. At least one clip is formed as a bent end sufficiently resilient for temporary unbending and displacement over and across the implanted lens peripheral edge to grip the clip thereon, e.g. with the clips being of selected length for maintaining the lens body optical axis concentric or eccentric to the implanted lens optical axis, the assembly upon insertion into the eye being clipped onto the implanted lens such that a bent end clip is last manipulated onto such peripheral edge.

U.S. Pat. No. 5,366,502 in its abstract describes a supplemental intraocular lens that is provided for either preoperative or postoperative attachment to a conventional implanted intraocular lens to provide an adjustable or removable multi-focal optic or to provide a necessary optic of spherical, cylindrical or combination shape for refractive error correction in aphakic patients. An intraocular lens system is also provided including a primary intraocular lens modified to provide for securing a supplemental corrective intraocular lens to the primary lens. Either the primary or supplemental lens could be formed of a suitable multi-focal lens, or both lenses could be mono-focal. The primary intraocular lens is implanted in the anterior chamber of an eye, or in the posterior chamber of an eye between the capsular bag and the iris.

WO2008094518 in its abstract describes a multi-component intraocular lens implanted in an optical system of a human eye, including one or more foldable removable components, each component being foldable. One component acts as a base lens, including a flange with an aperture or a slot. Another component acts as a mid lens and a third component acts as a top lens, which engages the mid lens. The top lens and mid lens may be joined to or integrated to form an optical assembly. The top lens, the mid lens or the optical assembly may include at least one projection that engages the slot of the base lens. A medical adhesive may be applied to an outer circumferential surface of the top lens to join the top lens to the mid lens or may be applied to a top surface of the top lens opposing a bottom surface of the mid lens. Because the lens components are foldable, they may be inserted into the eye using an incision smaller than the diameter of the unfolded lens. The removable components may be used to correct various medical conditions of the eye, as well as to improve and enhance vision, and for cosmetic purposes.

EP2422746 discloses according to its abstract an intraocular implant for placement in the eye, e.g. as part of a cataract operation or crystalline lens extraction refractive operation, has at a peripheral portion of the implant a groove which engages with the lip of a single capsulotomy only formed in the lens capsule of the eye. The implant will normally be a lens, but may instead be a bung or plug for occluding an opening made in the capsule. The groove may be a continuous groove around the periphery of the implant, or there may be a series of individual spaced-apart grooves formed as projections protruding from the periphery. Instead of a single groove, a pair of axially spaced-apart grooves may be provided, which engage with respective capsulotomies formed in an anterior and a posterior part of the capsule. The posterior groove is preferably of a smaller mean diameter than the anterior groove. The description shows an embodiment with "a series of projections projecting from the circumference of the lens portion", referring to very specific embodiments in the drawings.

WO2013112589 according to its abstract discloses a modular IOL system including intraocular primary and secondary components, which, when combined, form an intraocular optical correction device, wherein the secondary component is placed on the primary component within the perimeter of the capsulorhexis, thus avoiding the need to touch or otherwise manipulate the capsular bag. The secondary component may be manipulated, removed, and/or exchanged for a different secondary component for correction or modification of the optical result, on an intraoperative or post-operative basis, without the need to remove the primary component and without the need to manipulate the capsular bag. The primary component may have haptics extending therefrom for centration in the capsular bag, and the secondary component may exclude haptics, relying instead on attachment to the primary lens for stability. Such attachment may reside radially inside the perimeter of the capsulorhexis and radially outside the field of view to avoid interference with light transmission.

SUMMARY OF THE INVENTION

A disadvantage of prior art is that placement of the IOL, and in particular of secondary intraocular lenses, may be very difficult, with a high chance of damaging the capsular bag during the medical procedure. This is even more a problem if additional manipulations, for instance in the capsular bag, are required for correcting residual refractive errors.

Hence, it is an aspect of the invention to provide an alternative intraocular lens assembly, which preferably further at least partly obviates one or more of above-described drawbacks. In particular, the intra ocular lens assembly of the invention allows proper and straightforward placement. Alternatively or additionally, it induces less damage to the capsular bag and allows secure positioning.

The invention provides an intra ocular lens assembly comprising an intra ocular lens structure (IOL) for placement in the capsular bag and securing the IOL in an opening in an anterior part of a capsular bag, with an anterior capsular bag flap surrounding said opening, and a secondary intraocular lens (S-IOL) comprising fixing parts for attaching said S-IOL to said IOL.

In particular, said intra ocular lens assembly comprising an intra ocular lens structure (IOL) for placement in a capsular bag of an eye, said IOL comprising an optical structure comprising a perimeter, at least two posterior supports, coupled to and extending from said perimeter of said optical structure, for residing inside the capsular bag when the IOL is implanted in the capsular bag, and at least two anterior supports, coupled to and extending from said perimeter of said optical structure, for residing outside the capsular bag when the IOL is implanted in the capsular bag, the anterior supports and the posterior supports mutually positioned on said perimeter for holding an anterior capsular bag flap between them for securing the optical structure of the IOL aligned with an opening in an anterior part of the capsular bag.

In particular, said intra ocular lens assembly further comprising a secondary intra ocular lens (S-IOL) for attachment on an anterior side of the IOL, said S-IOL comprising a secondary optical structure comprising a secondary perimeter, and at least two fixing parts coupled with said secondary perimeter and each for coupling with one of said anterior supports, for fixing said S-IOL onto said IOL with the optical structure and the secondary optical structure aligned. In particular, the S-IOL comprises a ring about said secondary optical structure, with an inner perimeter of said ring attached to the secondary perimeter, said inner perimeter fitting about the perimeter of the optical structure of the IOL.

The IOL can be inserted into the capsular bag. The anterior and posterior supports allow fixing the IOL with its optical structure aligned with an opening, in particular an aperture or orifice, in a capsular bag. It was found that the IOL due to its possibility for stabile and accurate positioning with its optical structure positioned aligned with, more in particular in, the opening in the capsular bag provides a solid platform for additional refractive corrections.

The terms "anterior" and "posterior" relate to an arrangement of features relative to the propagation of the light into the eye. Thus, light enters through the cornea and passes the iris through the pupil. Cornea and iris are here considered anterior parts of the eye. Subsequently, the light propagates to the retina that is located in the posterior part of the eye.

The axis of an eye can be the optical axis, or can be the visual axis, the line of sight, or the pupillary axis. In FIG. 36, these axes are indicated.

An eye has a capsular bag that usually holds the natural lens. In conditions where that natural lens needs to be removed, an empty capsular bag remains. Usually, for removal of the natural lens, first an opening is made in the anterior part of the capsular bag. Part of the capsular bag membrane is removed. It leaves a through hole with a surrounded by a peripheral edge defining the perimeter. Such an opening can for instance be circular or elliptic. The anterior membrane of the capsular bag is thus provided with an aperture, providing an orifice that gives access to the capsular bag.

The part of the capsular bag that is closest to the cornea is here also referred to as the anterior capsular bag part. The remaining anterior capsular bag part that surrounds the mentioned opening is referred to as the anterior capsular bag flap. It can also be seen as a ring of capsular bag membrane.

The capsular bag also has a posterior part. That is the part of the capsular bag that is closest to the retina. The average capsular bag thickness is between 4 and 9 microns for the posterior capsular bag part and between 10 to 20 microns for the anterior capsular bag part.

In a procedure for removal of the natural lens, the opening in the anterior capsular bag can be made using a laser cutting device. This procedure for making the opening in the capsular bag is also referred to as capsulotomy. This laser-assisted procedure allows a very accurate positioning and shape of the opening in the capsular bag. Furthermore, after removal of the natural lens, it is possible to subsequently make an opening in the posterior part of the capsular bag, the posterior opening. These two openings can be accurately aligned. The shape of the openings can be matched with a shape of a perimeter of the IOL or, more exactly stated, a perimeter about the optical structure of the IOL. Thus, the IOL can fit in the opening perfectly. Finally, the openings can be matched perfectly with an optical axis of the eye. Furthermore, if an optical axis of the IOL is aligned in a predetermined position within the circumference of the IOL, the optical structure of the IOL can be positioned in an optimal manner in the eye. Thus, the optics of the optical structure can be aligned in a predefined manner in the eye. For instance, optical axes may be aligned, but also other predefined configuration may be possible, for instance taking into account the quality of parts of the retina.

In an embodiment, the assembly consists of the IOL and the S-IOL. The S-IOL functions as an additional correction on the IOL. In view of the accurate positioning and fixation of the IOL, it was found that further additional correction in this embodiment may not be needed. In fact, should additional correction be needed, then the S-IOL can be removed and another S-IOL can be inserted. Such an S-IOL may be customized or selected from a predefined set of S-IOLs.

The IOL has an anterior side, which is directed towards a cornea of the eye when the IOL is implanted in an eye and fixed to the capsular bag. The IOL further has a posterior side, which is directed towards a retina of the eye when the IOL is implanted in an eye and fixed to the capsular bag.

In an embodiment, the anterior supports and the posterior supports are mutually positioned on said perimeter for clipping an anterior capsular bag flap between them for securing the optical structure of the IOL in an opening in the anterior part of the capsular bag. This clipping prevents the IOL from independently moving in anterior and posterior direction in the eye. The supports work together to clip the optical structure in the opening in the anterior capsular bag part. In particular, this clipping also prevents rotation of the optical structure in the opening, for instance about an axis normal to the opening. In this sense, the word clipping is use to express holding sheet-like material in the way a paperclip clips onto one or more sheets of paper.

In order to clip the capsular bag flap, various mutual positions of the anterior and posterior supports can be considered. When the IOL is inserted into the capsular bag, the posterior supports remain inside the capsular bag. The anterior supports extend outside the capsular bag. The capsular bag flap is clamped between these supports. The anterior and posterior supports can be substantially in one plane. In such a configuration, in an embodiment, the supports are positioned staggered at the perimeter. For instance, when going around the perimeter, alternately an anterior support and a posterior support are provided. To provide additional clamping force, one or more anterior supports may incline in posterior direction, and/or one or more posterior supports may incline in anterior direction. This may be limited to less than about 10 degrees, more in particular to less than about 5 degrees.

Alternatively, or additionally, the anterior supports and the posterior supports may be at a distance from one another.

The anterior and posterior supports extend from the perimeter. In particular, the supports extend from the perimeter in a radial direction.

The perimeter of the optical structure can be a surface extending axially about the optical structure. The edge of the opening in the anterior capsular bag part can in such an embodiment fit around the perimeter of the optical structure. In an embodiment, taking into account the elasticity of the capsular bag, the perimeter of the opening can be smaller than the perimeter of the optical structure. The capsular bag flap thus fits tightly around the IOL.

Anterior and posterior supports of the IOL in an embodiment comprise support surfaces. The support surfaces can be bounded areas on the anterior respectively the posterior supports that engage the capsular bag surface. In an embodiment, at least one anterior support comprises a posterior side that substantially completely engages the anterior surface of the anterior capsular bag part. In an embodiment, at least one posterior supports comprise an anterior side that substantially completely engages the posterior surface of the anterior capsular bag part.

The invention further pertains to an intra ocular lens structure (IOL) for placement in the capsular bag and securing the IOL in an opening in an anterior part of a capsular bag, with an anterior capsular bag flap surrounding said opening, said IOL having an anterior side which in use when the IOL is implanted in an eye is directed towards a cornea of the eye, and a posterior side which in use when the IOL is implanted in an eye is directed towards a retina of the eye, said IOL comprising:
  an optical structure;
  at least two posterior supports for when the IOL is implanted in the capsular bag residing in the capsular bag and extending away from said optical structure, said posterior supports adapted for in use providing support surfaces for engaging a posterior surface of an anterior capsular bag flap, and
  at least two anterior supports for when the IOL is implanted in the capsular bag residing outside the capsular bag and extending away from said optical structure, said anterior supports adapted for in use providing support surfaces for engaging an anterior surface of an anterior capsular bag flap,
wherein a posterior plane defined by the support surfaces of the posterior supports and an anterior plane defined by the support surfaces of the anterior supports are adapted for in use being spaced apart at a distance adapted for holding an anterior capsular bag flap between them for securing the IOL in said opening.

In an embodiment, the IOL is formed as one part. In an embodiment, the IOL is made from a polymer material. In an embodiment, the IOL is foldable. The polymer material allows the IOL to be rolled into a roll with a diameter smaller than 2.5 mm. In order to allow clamping of the anterior capsular bag part, at least the anterior supports are resilient, allowing the IOL to be inserted in the capsular bag and subsequently bringing the anterior supports through the opening in the anterior capsular bag part and in engagement with the anterior surface thereof. In fact, this allows holding the IOL in place.

In an embodiment, the at least two posterior supports extending away from said optical structure are in a functionally opposite direction with respect to one another. In an embodiment, the at least two anterior supports extending away from said optical structure in a functionally opposite direction with respect to one another.

In an embodiment, the anterior plane and said posterior plane are, in particular in use when clamping the capsular bag, spaced apart 5-100 micron. In particular, said posterior and anterior planes are spaced apart 5-50 micron.

In case the support surfaces run about parallel, this distance allows a clamping of the anterior capsular bag flap.

The posterior supports, or at least their support surfaces, may be angled towards the anterior side of the IOL. In that way, after implantation in the capsular bag, the posterior supports can urge against the posterior surface of the capsular bag flap. The posterior supports can be at an angle of up to 10°.

Alternatively or in combination, the anterior supports, or at least their support surfaces, may be angled towards the posterior side of the IOL. In that way, after implantation in the capsular bag, the anterior supports can urge against the anterior surface of the capsular bag flap. The anterior supports can be at an angle of up to 10°.

In an embodiment, the posterior supports and the anterior supports are in perimetrical sense or azimuthal direction shifted with respect to one another. This allows an easier manufacturing, in particular using for instance tooling or moulding technology.

In an embodiment, the posterior supports and said anterior supports extend in perimetrical direction or in azimuthal direction about the optical structure. Thus, a good support of the capsular bag flap can be provided, and even a fixation of the IOL.

In an embodiment, the posterior supports and the anterior supports do not overlap. In fact, when viewed from the anterior side, if the anterior and posterior supports do not overlap, tooling can be simplified. Furthermore, it may even be possible to allow a smaller distance between the anterior and posterior planes. In fact, the support surface of the anterior support may be shifted to −100 micron past the support surface of the posterior support. In particular, shifted −70 micron past the support surface of the posterior support. In particular when the posterior support and the anterior support are resilient, the posterior support and the anterior support may clamp the capsular bag flap between them, thus fixing the IOL in the opening. Thus, when the supports do not overlap, the distance between the anterior and posterior plane can be between −100, in particular −70, and 100 micron. The negative values indicate that when not in use, the anterior support may be places further in posterior direction, past the posterior support. In use however, when holding the capsular bag, the anterior support will be at the anterior side of the anterior part of the capsular bag, and the posterior support will be at the posterior side of the anterior part of the capsular bag.

In an embodiment, the IOL comprises a perimetrical surface surrounding said optical structure and said posterior support and said anterior support extending from said perimetrical surface. In particular, said perimetrical surface defines a radial surface for when implanted engaging a perimetrical edge of the anterior capsular bag flap which defines the perimeter of the opening.

This can provide alignment of the IOL. For instance, if the opening is non-circular, for instance elliptic, and the perimeter of the IOL matches the shape of the opening, the azimuthal orientation of the IOL can be fixed. Thus, specific optical structures can be aligned.

In an embodiment, at least one selected from said posterior supports and said anterior supports is a haptic. In particular, the haptic has an outer diameter of 8-12 mm.

It was found that the IOL thus fits in the capsular bag. It may function as a fail-safe if aligning with the opening fails.

In an embodiment, the IOL is formed in one piece, its thickness and flexibility adapted for insertion of the IOL into the eye in a folded manner via a micro insertion.

In an embodiment, the IOL further comprises an at least partially peripheral groove posterior to the posterior supports. In particular, said posterior groove opens in radial direction for receiving, when said IOL is implanted in an eye, at least an edge of a posterior capsular bag flap surrounding a posterior opening in a posterior part of the capsular bag. In an embodiment, the posterior groove is between 0.1 and 0.3 mm deep. In particular said posterior groove is between 0.05-0.2 mm wide. More in particular, the posterior groove is tapered.

In an embodiment, said S-IOL comprises a posterior side facing the anterior side of said IOL, said anterior side of said IOL in use facing an iris of an eye, said ring comprises a posterior surface for engaging the anterior surface of the anterior capsular bag part, in particular said posterior surface axially positioned to at least be in plane with posterior surfaces of the at least two anterior supports, or positioned in posterior direction behind the posterior surfaces.

In an embodiment, said at least two fixing parts are attached to said ring, in particular said fixing parts extending from said posterior side of said ring.

In an embodiment, said at least two fixing parts are attached to said ring and extend in posterior direction beyond the posterior surface of said ring, in particular said fixing parts extend in posterior direction beyond a posterior surface of the anterior support they are coupled with.

In an embodiment, said anterior supports comprise through holes or openings, and said fixing parts comprise ends provided with patches or holding patches adapted for passing through said openings.

In an embodiment, said inner perimeter of said ring comprises a inner peripheral surface which runs conical, and said perimeter having a conical surface having substantially the same angle as the conical inner peripheral surface, said conical surfaces tapering in anterior direction.

In an embodiment,
said at least two posterior supports comprise closed loops which extend from said optical structure, and each loop has both ends attached to said perimeter, and
said at least two anterior supports are each positioned within one of said loops between said ends.

In an embodiment, said posterior supports and said anterior supports of the IOL are in azimuthal sense (Az) shifted or staggered with respect to one another.

In an embodiment, said posterior supports of the IOL provide anterior support surfaces and said anterior supports of the IOL provide posterior support surfaces that are in azimuthal sense (Az) shifted or staggered with respect to one another, in particular providing in azimuthal sense (Az) each time a posterior support surface and an anterior support surface.

In an embodiment, said posterior supports and said anterior supports of the IOL extend in azimuthal sense (Az) about the optical structure.

In an embodiment, an anterior side of said optical structure and a posterior side of said secondary optical structure facing said optical structure have substantially the same radius of curvature, in particular said anterior side of said optical structure and a posterior side of said secondary optical structure comprise a spacing.

The invention further relates to an intra ocular lens structure (IOL) for placement in the capsular bag, comprising:—an optical structure comprising a perimeter;
at least two posterior supports, coupled to and extending from said perimeter of said optical structure, for residing inside the capsular bag when the IOL is implanted in the capsular bag, and at least two anterior supports, coupled to and extending from said perimeter of said optical structure, for residing outside the capsular bag when the IOL is implanted in the capsular bag, the anterior supports and the posterior supports mutually positioned on said perimeter for clipping an anterior capsular bag flap between them for securing the optical structure of the IOL aligned with an opening in an anterior part of the capsular bag.

The invention further relates to a secondary intra ocular lens (S-IOL), said S-IOL comprising:
a secondary optical structure;
a ring attached about said secondary optical structure, said ring comprising at least two axial surfaces;
at least two fixing parts extending from said axial surfaces of said ring and holding patches at their ends at a distance from the axial surfaces of the ring.

The invention further relates to a method for fixing the intra ocular assembly of any one of the preceding claims into an eye, the method comprising:
forming an opening in an anterior part of a capsular bag of an eye, in particular performing a laser-assisted capsulotomy, said opening surrounded by an anterior capsular bag flap remaining after forming said opening;
removing a natural lens from the capsular bag through said opening;
inserting the IOL in the capsular bag through said opening;
taking the anterior supports out the capsular bag while leaving the posterior supports inside the capsular bag, thereby securing the IOL aligned in the opening of anterior part of the capsular bag.

In an embodiment, the method comprises colouring the anterior part of the capsular bag with a light absorbing composition having absorption properties selected in order to absorb the laser beam energy.

In an embodiment, said opening is positioned in alignment with an axis of the eye and/or with the optical structure of the IOL.

In an embodiment, said opening is positioned in alignment with an optical and azimuthal axis of the eye and an optical and azimuthal axis of the optical structure of the IOL.

In an embodiment, said opening is circular with a centre aligned with the optical axis of the eye, and the optical structure comprises an optical axis that is aligned with the perimeter of the IOL.

In an embodiment, said opening is non-circular, and said perimeter of said optical structure is circular. This allows applying a tilt to the optical structure with respect to an axis of the eye.

In an embodiment, the method further comprises subsequently inserting an S-IOL in said eye.

In an embodiment, the method further comprising coupling the fixing parts to corresponding anterior supports.

The invention further pertains to a method for fixing the intra ocular structure (IOL) described above into an eye, where the IOL has a perimeter about an optical structure, the method comprising:
forming an opening within the anterior part of a capsular bag of an eye, the opening having a profile matching the perimeter of the IOL, said opening surrounded by an anterior capsular bag flap remaining after forming said opening;
inserting the IOL in the eye with the posterior supports extending in said capsular bag, and
taking the anterior supports out the capsular bag with the anterior support surfaces resting on the anterior surface of the remaining anterior part of the capsular bag surrounding said opening and while leaving the posterior supports inside the capsular bag, the remaining part of the anterior part of the capsular bag surrounding the opening positioned between the posterior and anterior supports, thereby securing the IOL in the opening of anterior part of the capsular bag.

In an embodiment of the method, the opening is aligned with an axis of the eye and/or with the optical structure of the IOL. In case the optical structure is a lens, often an optical axis of this lens is aligned.

In an embodiment of the method, the opening is aligned with an axis and/or an azimuthal axis of the eye and an optical and/or azimuthal axis of the optical structure of the IOL.

In an embodiment of the method, the opening is circular with a centre aligned with an axis of the eye, and/or the optical structure comprises an optical axis that is aligned with the perimeter of the IOL.

In an embodiment of the method, the perimeter is circular.

In an embodiment of the method, the capsular bag further comprises a posterior part, said method further comprise:
forming a posterior opening in the posterior part of the capsular bag, said posterior opening surrounded by an posterior capsular bag flap remaining after forming said posterior opening;
applying an edge of the posterior capsular bag flap that surrounds the posterior opening in a posterior groove in the IOL and which at least partially surrounds the optical structure posterior of the posterior supports. Thus the posterior capsular bag flap is secured to the IOL, posterior to the posterior supports.

The invention further relates to an intra ocular lens assembly comprising an intra ocular lens structure (IOL) for placement in a capsular bag of an eye, said IOL comprising:
an optical structure comprising a perimeter;
at least two posterior supports, coupled to and extending from said perimeter of said optical structure, for residing inside the capsular bag when the IOL is implanted in the capsular bag, and
at least two anterior supports, coupled to and extending from said perimeter of said optical structure, for residing outside the capsular bag when the IOL is implanted in the capsular bag, the anterior supports and the posterior supports mutually positioned on said perimeter for holding an anterior capsular bag flap between them for securing the optical structure of the IOL aligned with an opening in an anterior part of the capsular bag, said intra ocular lens assembly further comprising a secondary intra ocular lens (S-IOL) for attachment on an anterior side of the IOL, said S-IOL comprising:
a secondary optical structure comprising a secondary perimeter, and
at least two fixing parts, coupled said secondary perimeter and each for coupling with one of said anterior supports, for fixing said S-IOL onto said IOL with the optical structure and the secondary optical structure aligned.

The S-IOL in an embodiment further comprises positioning parts comprising radial surfaces for engaging the perimeter of the IOL, and axial surfaces in an axial surface plane parallel to a plane of posterior surfaces of the anterior supports and axially positioned in plane or displaced in posterior direction, said positioning parts attached to the S-IOL outside the secondary perimeter.

In an embodiment, the IOL comprises an indentation in said perimeter, providing an axially extending groove in the peripheral surface of said perimeter.

In an embodiment, this indentation is provided between a posterior support and an anterior support. When positioned in the opening of the capsular bag, as explained the peripheral edge of the capsular bag will rest around the perimeter of the IOL. The indentation will then provide a passage for fluid which allows fluid communication through the eye.

In an embodiment, the S-IOL comprises a passage extending though said S-IOL and connecting to said indentation of the IOL. When the S-IOL is positioned on the IOL, there will remain one or more passages for liquid, allowing an exchange of liquid from the anterior side of the capsular bag into the capsular bag and even to the posterior side of the capsular bag.

In an embodiment, the S-IOL comprises an indentation in its perimeter providing a radially extending groove connecting to said indentation of said IOL. In this embodiment, again a passage for fluid is provided past at least one membrane of the capsular bag.

The invention further relates to an intra ocular lens assembly comprising an intra ocular lens structure (IOL) for placement in the capsular bag and securing the IOL in an opening in an anterior part of a capsular bag, with an anterior capsular bag flap surrounding said opening, and a secondary intraocular lens (S-IOL) comprising fixing parts for attaching said S-IOL to said IOL.

The invention further relates to an intra ocular lens assembly comprising an intra ocular lens structure (IOL) for placement in a capsular bag of an eye, said IOL comprising an optical structure comprising a perimeter, at least two posterior supports, coupled to and extending from said perimeter of said optical structure, for residing inside the capsular bag when the IOL is implanted in the capsular bag, and at least two anterior supports, coupled to and extending from said perimeter of said optical structure, for residing outside the capsular bag when the IOL is implanted in the capsular bag, the anterior supports and the posterior supports mutually positioned on said perimeter for holding an anterior capsular bag flap between them for securing the optical structure of the IOL aligned with an opening in an anterior part of the capsular bag, said intra ocular lens assembly further comprising a secondary intra ocular lens (S-IOL) for attachment on an anterior side of the IOL, said S-IOL comprising a secondary optical structure comprising a secondary perimeter, and at least two fixing parts, coupled with said secondary perimeter and each for coupling with one of said anterior supports, for fixing said S-IOL onto said IOL with the optical structure and the secondary optical structure aligned.

The term "substantially" herein, such as in "substantially opposite" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" herein, such as in "functionally opposite", will be understood by the person skilled in the art. It includes for instance exactly opposite, but deviations from exact positioning are also included, as long as in operation, the feature functionally behaves or has the effect of being for instance substantially opposite. The term "functionally" may therefore also include embodiments with "entirely", "completely", "all", etc. Hence, in embodiments the adjective functionally may also be removed. Where applicable, the term "functionally" may also relate to 90% or higher, such as 95% or higher, especially 99% or higher, even more especially 99.5% or higher, including 100%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements.

The mere fact that certain measures are recited in mutually different dependent claims does not indicate that a combination of these measures cannot be used to advantage. In fact, many of the features of the current IOL, S-IOL or the assembly can be combined to further improve easy implantation, or fixation.

The invention further applies to an apparatus or device comprising one or more of the characterising features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 1 schematically depicts an embodiment of an IOL in anterior view;

FIG. 2 shows the embodiment of FIG. 1 in side view;

FIG. 3 shows a detail of FIG. 2 as indicated;

FIG. 6A shows a cross section of the IOL of FIG. 1 with the posterior feature of FIG. 1;

FIG. 6B shows a cross section of the IOL of FIG. 5 with the alternative posterior feature;

FIG. 7A shows a detail of FIG. 6A as indicated;

FIG. 7B shows a detail of FIG. 6B as indicated;

FIG. 17 shows a cross section of FIG. 12 as indicated;

FIG. 18 shows a detail of FIG. 15 as indicated;

FIG. 27 shows a cross sectional view of the intra ocular lens assembly of FIG. 12 fixed to an anterior capsular bag part, showing the flexible clamping using the anterior capsular bag part;

FIG. 28 shows a front view or anterior side of the alternative IOL of FIGS. 4 and 5 with an alternative secondary intraocular lens (S-IOL) attached to it;

FIG. 29 shows the posterior side of the assembly of FIG. 28;

The drawings are not necessarily on scale.

DESCRIPTION OF PREFERRED EMBODIMENTS

In this description, first relevant parts of the eye will be described in FIGS. 39A and 39B and 39C. In FIGS. 1-11, some particular embodiments of an intraocular lens structure (IOL) and its position in an eye (FIGS. 9-11) will be described, and a procedure for placing such an IOL in an eye. In FIGS. 12-35, some embodiments of an intraocular lens assembly will be described which are based upon the IOL described in FIGS. 1-11.

The Eye

Figures 39A, 39B:
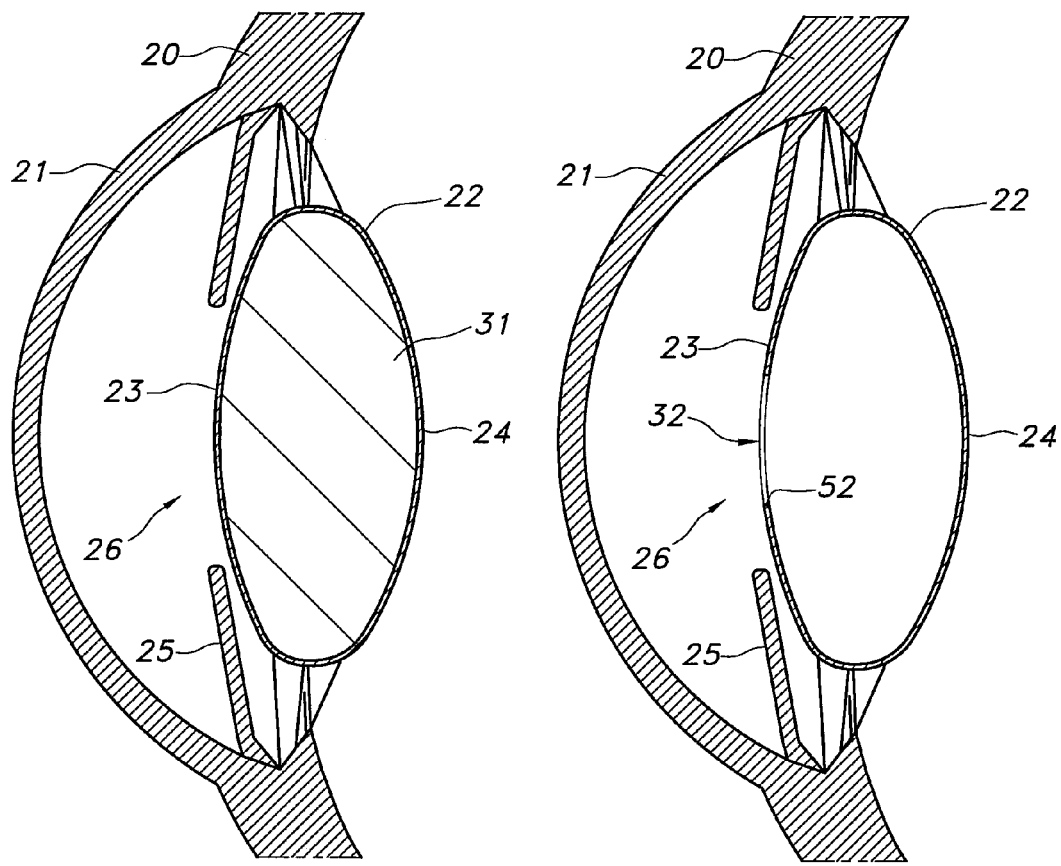
FIGS. 39A and 39B schematically indicate a cross section through an eye before and after removal of the natural lens, and FIG. 39C a front view of FIG. 39B.
Figure 39C:
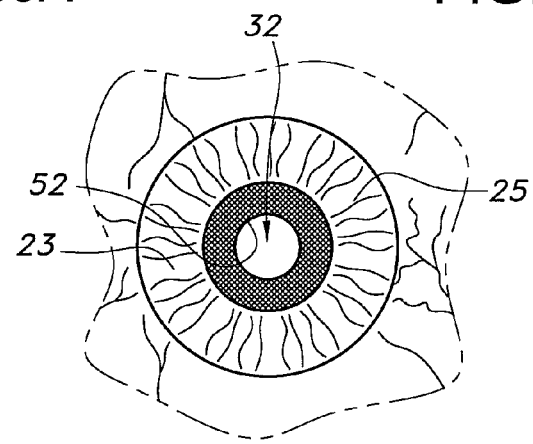

In FIGS. 39A and 39B, schematically a cross section through an eyeball 20 is depicted. In FIG. 39A, the eyeball 20 has a cornea 21, iris 25, pupil 26, and capsular bag 22 with a natural lens 31. The capsular bag 22 has an anterior part 23 and a posterior part 24. In FIG. 39B, the eyeball 20 is shown after the natural lens 31 has been removed, leaving the empty capsular bag 22 with an opening 32, usually having a circular or an elliptic shape. The opening 32 is in the anterior part 23 of the capsular bag 22. In many cases, the centre of the opening 32 will be on an axis of the eye. The axis are defined in FIG. 36. FIG. 39C shows part of the eyeball in front view, showing the iris 25, the anterior part 23 of the capsular bag with opening 32 and the edge of the opening 52. This edge 52 is also referred to as the 'perimetrical edge' 52.

In some patients, the posterior part 24 of the capsular bag 22 may not be clear anymore. In these cases or to generally avoid post surgery posterior capsular opacification, additionally an opening in the posterior part 24 or the capsular bag 22 may be made, referred to as the posterior opening, or the posterior part 24 of the capsular bag may be removed.

In the previous paragraph, the adjectives 'anterior' and 'posterior' are used. As explained before, the terms "anterior" and "posterior" relate to an arrangement of features relative to the propagation of the light into the eye. Thus, light enters cornea and iris, which are anterior parts of the eye, and propagates to the retina that is located in the posterior part of the eye. Thus, for instance the capsular bag 22 has an anterior part 23 and a posterior part 24. The anterior part, in turn, has a surface directed towards the cornea 21 and the iris 25. This surface will be referred to as the anterior surface of the anterior part 23 of the capsular bag 22. The opposite surface, at the inside of the capsular bag 22, will thus be referred to as the posterior surface of the anterior part 23 of the capsular bag 22.

The Intraocular Lens Structure (IOL)

Next, some embodiments of the intraocular lens structure (IOL) will be described. FIG. 1 schematically depicts an embodiment of an intra ocular lens structure (IOL) 1 in anterior view. The anterior side is the side of the IOL 1 that is directed towards the cornea 21 when said IOL 1 is placed in an eye. The side of the IOL 1 that is directed towards the retina after the IOL is implanted in an eye is here referred to as the posterior side of the IOL 1. When a natural lens 31 has to be removed from an eye, usually an opening 32 is made in the anterior part 23 of the capsular bag 22. Subsequently, the natural lens 31 is removed. In specific cases, such as paediatric patients, there may also be a posterior opening made in the posterior part 24 of the capsular bag 22, the part of the capsular bag 22 that is positioned between the natural lens 31 and the retina. The opening 32 and the posterior opening are usually aligned. The openings are often circular, but other shapes may be possible, certainly when using laser-assisted capsulotomy. The openings are usually aligned with an optical axis of the eye, but other positions maybe used. Around the openings, a ring of capsular bag tissue or membrane remains. This ring is also referred to as a capsular bag flap. The ring or flap has an edge bounding the perimeter of the opening 32, or in fact defining the opening 32. The opening 32 has a radial direction, running from the centre of the opening 32 outwards to its perimeter.

The IOL 1 comprises an optical structure 2. The optical structure 2 in many cases is a lens, in fact an anterior lens and a posterior lens. In embodiments like the one shown in FIG. 1, the optical structure 2 has an anterior lens structure surface 3 and a posterior lens structure surface 4, see FIG. 2. The optical structure can further be provided with any type of optical structure known in IOLs. In this description, the nature of the optical structure should further not be considered limited. The optical structure can comprise a lens or a closure cap. In an embodiment, both the anterior and posterior sides are provided with a curved surface to provide one or more lenses. Examples of lens optics are a mono focal lens, an astigmatic lens, a multifocal lens, an accommodative lens or a sector bifocal such as for instance disclosed in WO2012/118371, which is incorporated by reference as if fully set forth. The optics may be refractive, diffractive, or a combination of both. Furthermore or in combination, the optical structure may comprise an optical filter, and/or a functional layer known to a skilled person. The optical structure may comprise active and/or passive elements. An example of an active element is for instance an liquid crystal optics.

An IOL 1 usually is substantially a flat structure. Its thickness is about 0.1-1 mm. The diameter of IOL 1 usually is about 7-12 mm. The optical structure usually has a diameter of between 4-7 mm. In most embodiments, the optical structure has a diameter of 5-7 mm. The optical structure often is biconvex.

In such a mainly flat structure, an axial sense Ax can be distinguished which can have a posterior direction and an anterior direction. Furthermore, a radial sense Ra can be distinguished. Finally, an azimuthal sense Az can be distinguished, which can have a clockwise and counter clockwise direction. In case the optical structure is a simple, circular lens, the axial sense is the optical axis, and the radial sense is the radial direction of the lens. In FIGS. 1 and 2 these are indicated. In case of other optical structures, the axial, radial and azimuthal sense will be clear to a skilled person.

In an embodiment, the IOL 1 is made from a polymer material. In particular, the IOL 1 is from a polymer material that is foldable. In particular, the supports are resilient. The IOL 1 in an embodiment is made in one piece. In particular. The IOL 1 is pliable to allow it to be rolled up in a small roll with a diameter smaller than 2.5 mm. In particular, it allows rolling the IOL up to a diameter smaller than 1.8 mm. On the other hand, the IOL is dimensionally stable, in particular flexible to be able to unfold from its rolled-up state and to return to its original shape once it is inserted in the capsular bag.

Figure 4:
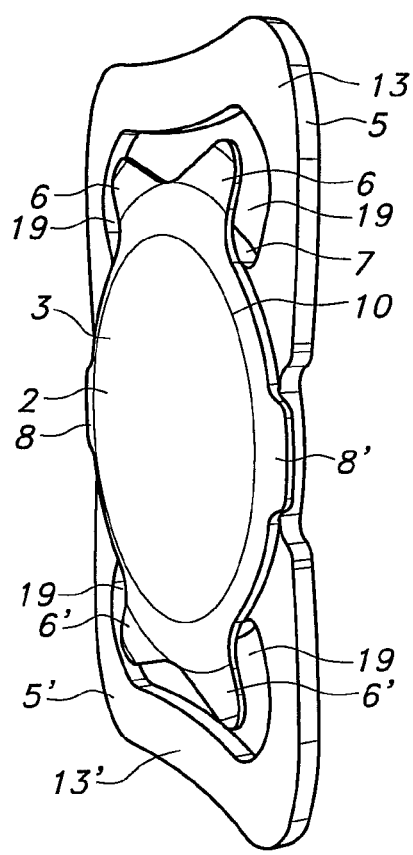
FIG. 4 shows the embodiment of FIG. 1 in perspective view showing the anterior side.

The embodiment of FIG. 1 is further also shown in detail in FIGS. 2-4, in which FIG. 2 shows the embodiment of FIG. 1 in side view, FIG. 3 shows a detail of FIG. 2 as indicated in FIG. 2, and FIG. 4 shows the embodiment of FIG. 1 in perspective view, from the anterior side.

The IOL comprises a perimeter 7 about the optical structure 2. The perimeter 7 has a perimetrical surface. The perimeter 7 can match the shape of the opening in the capsular bag. If for instance the opening is circular, the perimeter can be circular. The size of the perimeter is such that it may be a little oversized to stretch the size of the capsular opening a little or matches the size of the opening. In the embodiment of FIG. 1, the optical structure 2 comprises a curved surface providing a lens. The lens in this embodiment is circular and has an optical axis. The perimetrical surface here extends parallel to the optical axis. The perimeter provides here a cylindrical surface. In case of a circular perimeter 7, the perimetrical surface is circle cylindrical, in the embodiment of FIG. 1 even right circle cylindrical. A non-circular shape of the opening and the perimeter 7 can have advantages for preventing rotation of the IOL 1 about the optical axis. For instance, the opening can be elliptical, and the perimeter 7 can be elliptical, matching the elliptical shape of the opening. Alternatively, an alignment feature, for instance a cam, can be provided at the perimeter 7, and a matching feature can be provided to the opening. The rotational fixation can for instance be advantageous in case of astigmatic optics. It an embodiment, for instance shown in FIG. 1 and FIG. 8, the diameter of perimeter 7 is larger than the perimeter 10 of the optical structure 2. Perimeter 7 can for instance be 0.5-2 mm larger than perimeter 10 of the optical structure 2.

The IOL 1 comprises posterior supports 5, 5' here at opposite sides of the optical structure 2. The posterior supports 5, 5' extend away from the optical structure. In particular, the posterior supports 5, 5' extend away in sideward direction with respect to the optical structure 2. The posterior supports 5, 5' have support surfaces 13, 13', also referred to as the support surfaces of the posterior supports 5, 5'. These support surfaces 13, 13' are here in a plane, referred to as the posterior plane. In the specific embodiment of FIG. 1, where the perimeter discussed above is cylindrical, the posterior plane is perpendicular to the cylindrical surface of the perimeter 7.

The posterior supports 5, 5' here form loops that have two ends attached to the perimeter 7.

The optical structure 2 usually has a diameter of between 4-7 mm. The perimeter 7 usually has a diameter of between 4-7 mm. In the embodiments shown in the drawings, the anterior supports 6, 6' and the posterior supports 5, 5' are attached to the perimeter 7.

When the IOL 1 is implanted, the support surfaces 13, 13' of the posterior supports 5, 5' engage the posterior surface of the anterior part 23 of the capsular bag 22. In an embodiment, the posterior supports 5, 5' and thus at least part of the support surfaces can be angulated between 0-10 degrees in anterior direction. In an embodiment, when implanted, the surface of perimeter 7 engages or almost engages the edge of the opening in the anterior capsular bag, and the support surface 13, 13' of the posterior supports 5, 5' in fact nestles against the posterior surface of the anterior capsular bag. To that end, the support surface 13, 13' can be adapted to hold the surface of the capsular bag. For instance, cams or rims may be provided.

At least one of the surfaces of the posterior supports can be roughened, for instance sand blasted, in order to prevent reflections of light.

The IOL 1 further comprises anterior supports 6, 6'. The anterior supports 6, 6' also extend sideward with respect to the optical structure 2. The anterior supports provide the support surfaces 14, 14' of the anterior supports 6, 6'. When the IOL 1 is implanted, these anterior supports 6, 6' are outside of the capsular bag 22. The support surfaces 14, 14' are designed and adapted for, when the IOL 1 is implanted, engaging the anterior surface of the anterior part of the capsular bag. Again, these support surfaces 14, 14' are in a plane, referred to as the anterior plane. In an embodiment, when implanted, the surface of perimeter 7 engages or almost engages the edge of the opening in the anterior capsular bag, and the support surface 14, 14' of the anterior supports 5, 5' in fact can be made to nestle against the anterior surface of the anterior capsular bag. Both surfaces are thus in almost complete physical contact. To that end, the support surface 14, 14' can be adapted to hold the surface of the capsular bag. For the anterior supports to actually reach outside the capsular bag and be able to nestle against the anterior surface of the anterior capsular bag, usually requires some manipulation of the person implanting the IOL 1.

The anterior plane is functionally parallel to the posterior plane. Side view FIG. 2 shows this. In particular, these planes are parallel when holding the capsular bag 22 between them. The distance between the posterior support surfaces 14, 14' of the anterior support 6, 6' and the anterior support surfaces 13, 13' of the posterior support 5, 5' are such that they can hold the anterior part 23 of the capsular bag 22 between them. The anterior supports 6, 6' and the posterior supports 5, 5, are positioned such that their support surfaces comprise a spacing 11 between them. In fact, the distance between the posterior plane and/or the anterior plane is adapted for holding the anterior capsular bag flap 23 between them for securing the IOL 1 in the opening when the IOL 1 is implanted. In fact, the distance between the posterior plane and the anterior plane can be adapted to the thickness of the anterior part of the capsular bag. It was found that the posterior supports 5, 5' and the anterior supports 6, 6' were able to hold the anterior capsular bag flap between them if the distance is between 5 and 100 microns. In particular, the posterior plane and the anterior plane are spaced apart 15-50 microns. The distance provides the spacing 11. In case the distance is less than 20 microns the flap will be securely clamped and possible rotation of the lens prevented.

In the embodiment of FIG. 1, the posterior supports 5, 5' and the anterior supports 6, 6' are staggered. In fact, when viewed from the anterior direction, the posterior supports 5, 5' and the anterior supports 6, 6' do not overlap. This may also be referred to as that the posterior supports 5, 5' and the anterior supports 6, 6' are staggered in a perimetrical sense or azimuth sense (Az, FIG. 1). In this sense, staggered is used as in a 'staggered junction'.

In particular, when the posterior supports 5, 5' and the anterior supports 6, 6' are staggered, the posterior plane and the anterior plane are parallel or substantially parallel when the anterior part of the capsular bag is held between them.

In the embodiment of FIG. 1, the posterior supports 5, 5' of IOL 1 are closed loops. In the embodiment of FIG. 1, the posterior supports 5, 5' of IOL 1 have a diameter of about 7-12 mm. A thickness of the posterior support can be between 0.15-0.4 mm. In particular, the thickness can be between 0.20-0.35 mm.

Alternatively, the ends of the loops may also be removed, turning posterior supports 5, 5' in fact each into two posterior supports, resulting in four posterior supports 5, 5'. The radially extended posterior supports or loop supports may in fact act as safeguard if placement of IOL 1 in the opening 32 can not be accomplished for some reason.

The thickness of the anterior supports 6, 6' can be between 0.04 and 0.25 mm. In particular the thickness can be between 0.05 and 0.20 mm.

In the embodiment of FIG. 1, the IOL 1 at or near the perimeter 7 has at least one in perimeter or azimuthal direction extending space 19 between a posterior support 5, 5' and an anterior support 6, 6'. This space facilitates manufacturing, and also facilitates getting the anterior support 6, 6' through the opening 32 and out of the capsular bag as it provides room for insertion of an instrument when inserting and positioning the IOL 1. In the embodiment of FIG. 1, at each transition from anterior support 6, 6' to posterior supports 5, 5' there is a azimuthal space 19.

It was found that in order to support the posterior side of the anterior part of the capsular bag, the posterior supports 5, 5' extend at least about 0.5 mm away from the perimeter, in radial direction. In particular, the posterior supports 5, 5' extend at least 1.0 mm in radial direction.

It was found that in order to support the anterior side of the anterior part of the capsular bag, at least one of the anterior supports 6, 6' extend at least about 0.3 mm away from the perimeter, in radial direction. In particular, the anterior supports 6, 6' extend at least 0.5 mm in radial direction.

In the embodiment of the IOL 1 of FIG. 1, the IOL 1 has additional anterior supports 8, 8'. These anterior supports are here referred to as anterior lips 8, 8'. These in use also extend outside the capsular bag 22. They complement the other anterior supports 6, 6' and provide additional clamping of the anterior capsular bag part 23. The anterior lips 8, 8' have posterior surfaces 17, 17' that rest against the outside of the capsular bag 22, against the anterior surface of the anterior capsular bag part 23. The anterior lips 8, 8' here extend in perimeter (or azimuthal) direction about 0.1-2 mm. The anterior lips 8, 8' extend in radial direction, i.e. away from the optical structure 2 and the perimeter 7, about 0.1-1.3 mm. In particular, they extend about 0.4-1.0 mm. In this embodiment, the anterior lips 8, 8' extend about 0.3 mm.

Figure 8:
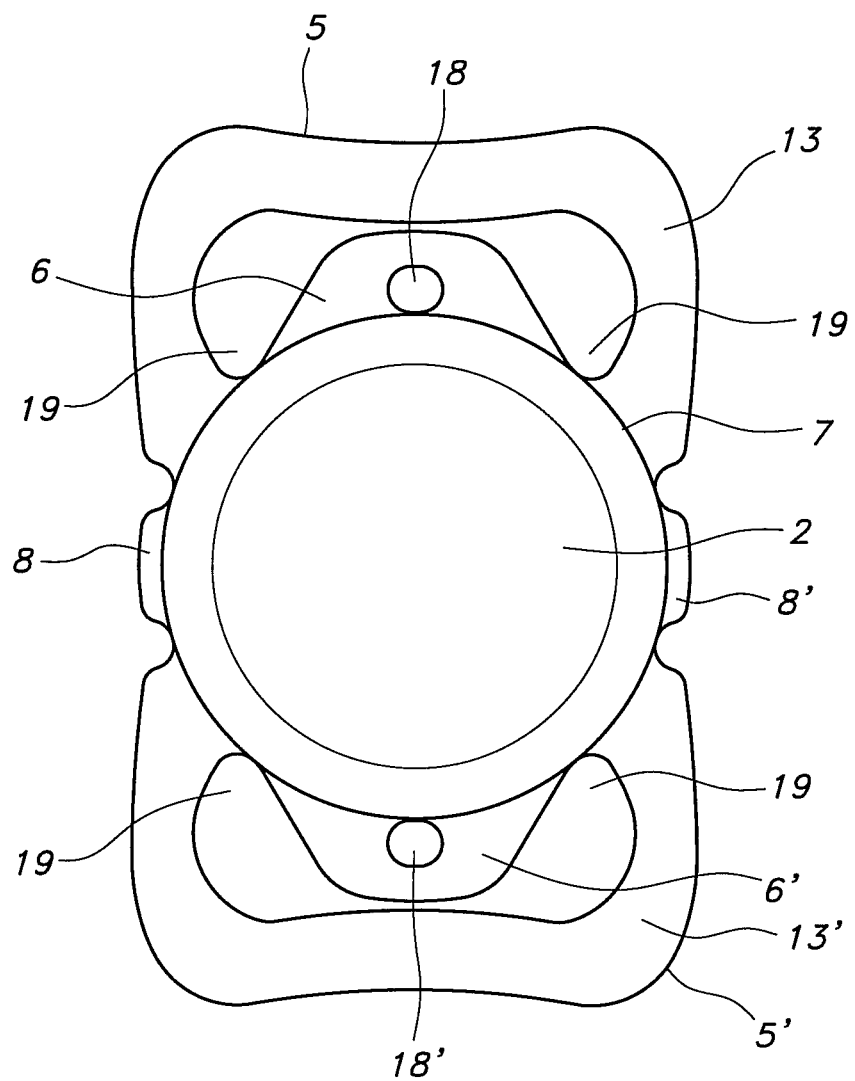
FIG. 8 shows yet another alternative embodiment of an IOL in anterior view.

In FIG. 8, an embodiment of an IOL 1 is shown in which the anterior supports 6, 6' have an alternative shape. In this embodiment, the anterior supports 6, 6' are provided with a support opening 18, 18'. Through these support openings 18, 18', an instrument can be inserted for pulling the anterior supports 6, 6' back through the opening 32 in the capsular bag after the IOL was inserted in the capsular bag. The anterior supports 6, 6' thus reach outside the capsular bag. The diameter of the support opening 18, 18' can be 0.2-1.5 mm.

In FIGS. 6A and 6B, two different embodiments of posterior features that influence the posterior part of the capsular bag can be seen.

Figure 5:
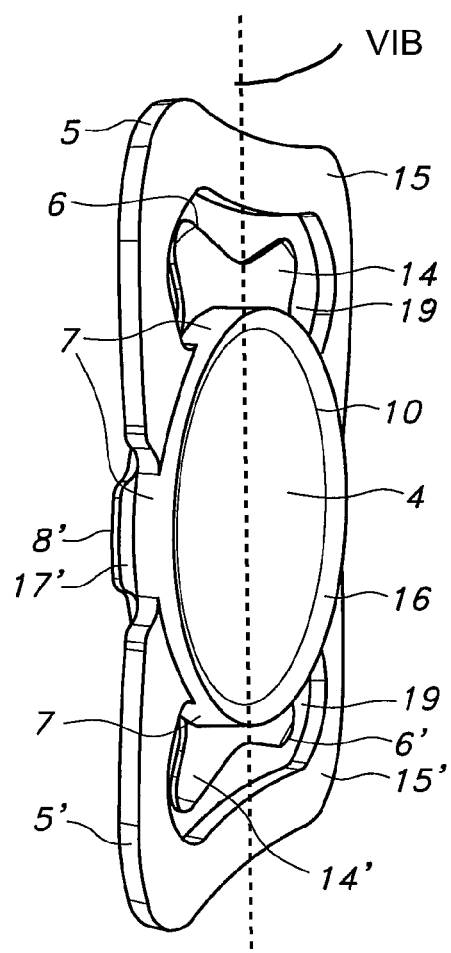
FIG. 5 schematically depicts a posterior side of the IOL of FIG. 1, with an alternative posterior feature.

In FIGS. 5, 6B and 7B, showing respectively a perspective view from the posterior side, a cross section and a detail of the cross section of FIG. 6B as indicated, the posterior side of the IOL 1 at and near the perimeter is provided with a sharp rim 16 to prevent growth of tissue from the posterior capsular bag part. Such growth of tissue can cause posterior capsul opacification.

In FIGS. 2, 3, 6A and 7A, an alternative embodiment of posterior features is shown. FIG. 2 shows a side view, FIG. 3 shows a detail as indicated, FIG. 6A shows a cross sectional view of the IOL of FIG. 1, and FIG. 7A shows a detail as indicated in FIG. 6A.

The IOL of this embodiment has a circumferential posterior groove 12, extending posterior to the posterior supports 5, 5' and the anterior supports 6, 6'. In fact, the posterior groove 12 is here provided posterior to the posterior surface 15, 15' of the posterior supports 5, 5'. The posterior groove 12 is provided to receive and hold the edge around the posterior opening, i.e., the opening in the posterior capsular bag. As explained, such a posterior opening can be made by a second capsulotomy performed on the posterior part 24 of the capsular bag 22. The edge around the posterior opening is slipped into posterior groove 12 after the IOL 1 is positioned in the opening in the anterior capsular bag part. To that end, the IOL can be gently urged backward until the edge or rim of the posterior opening slips into the posterior groove 12. The posterior groove 12 here has a depth of 0.1-0.3 mm. The posterior groove 12 is shaped to receive the edge around a posterior opening. The posterior groove 12 can be a rectangular groove. Here it is wedge-shaped. It has walls at an angle of between 10 and 60 degrees, in particular about 40-50 degrees. This posterior groove 12 will seal the posterior opening, preventing capsule opacification and/or leakage of the vitreous.

The IOL Positioned in the Eye

Figure 9:
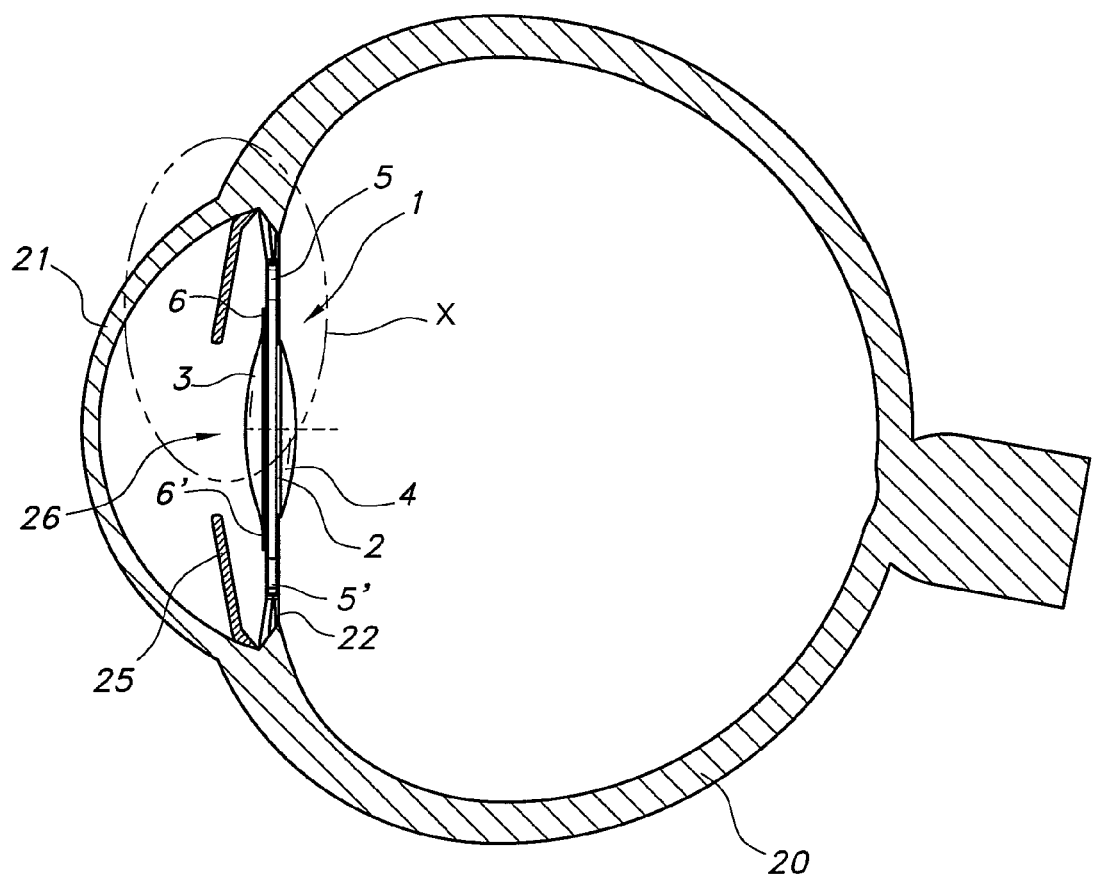
FIG. 9 shows an eyeball with an IOL.

FIG. 9 shows in cross sectional view an eyeball with an IOL 1 in inserted position inside capsular bag 22. The eyeball 20 has a cornea 21, an iris 25 with a pupil 26, and the capsular bag 22.

Figure 36:
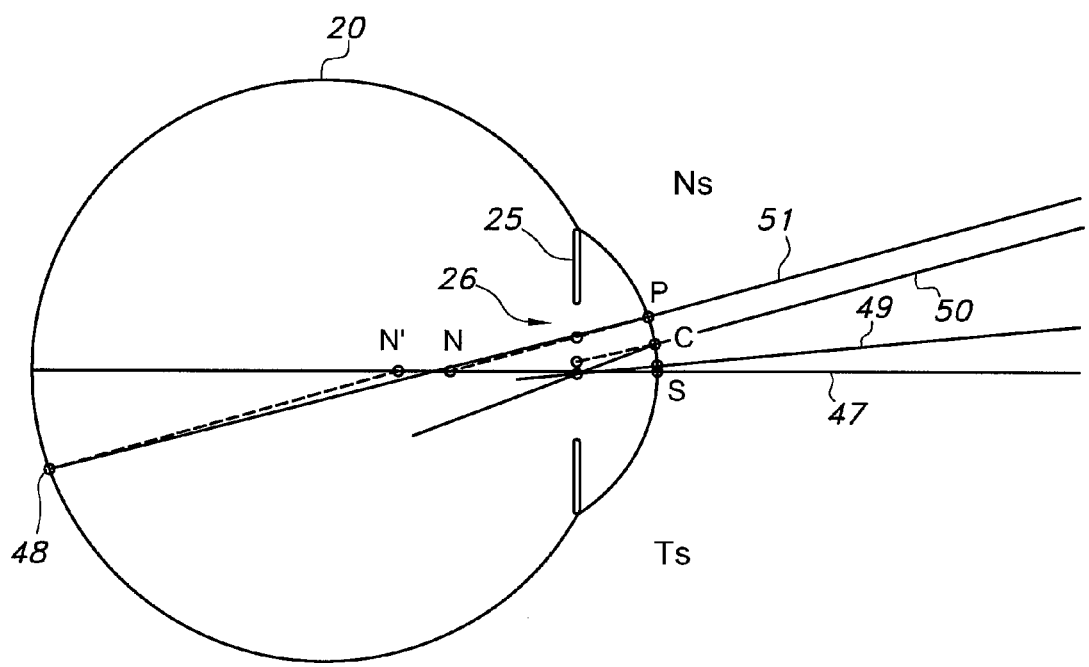
FIG. 36 an eye from above showing axes in the eye.

In FIG. 36, showing a cross section through the eye from above, several axes of the eye 20 are defined (Ns=Nasal side, Ts=Temporal side):

1. The visual axis 51, which goes through the fixed object point and the nodal point N of the eye. If the function of the nodal points is taken into account, the ray, which represents the visual axis 51, passes to the retina through the fovea 48.

2. The optical axis 47, which is perpendicular to the cornea surface and passes the iris 25 pupil 26 at the midpoint. Since the fovea 48 is not located central to the eyeball 20, the optical axis 47 differs from the visual axis 51. The optical axis 51 is the geometrical symmetry axis of the eye-ball system and is different from the optical central ray, which reaches the central point of the fovea and passes obliquely through the eye system.

3. The line of sight 50 is the axis, which goes through the object point and the centre of the entrance pupil 26. It is the ray, which passes through the centroid of the light bundle and is the axis of the ray cone, which enters the eye 20. Typically, the angle between the line of sight and the optical axis 47 lies in the range between 3° and 8°. The centre of the entrance pupil 26 is shifted towards the nasal side Ns due to the asymmetrical imaging through the cornea system and the off-axis position of the fovea. In the drawing, the temporal side (Ts) is also indicated.

4. The pupillary axis 49, which passes through the centre of the entrance pupil 26 and is perpendicular to the front surface of the cornea.

The field of view for monocular sight covers the whole retina without the small portion of the blind spot. Usually humans tend to rotate the eye to the most favourable position where the image is generated in the fovea 48. If the eye 20 is moved in this way into a position of optimal orientation so that the image is in the central part of the fovea, the optical system of the eye is not used as a centered system. Nevertheless, the tilt is small and spherical aberration and astigmatism are the dominating aberrations of the eye.

Figure 10:
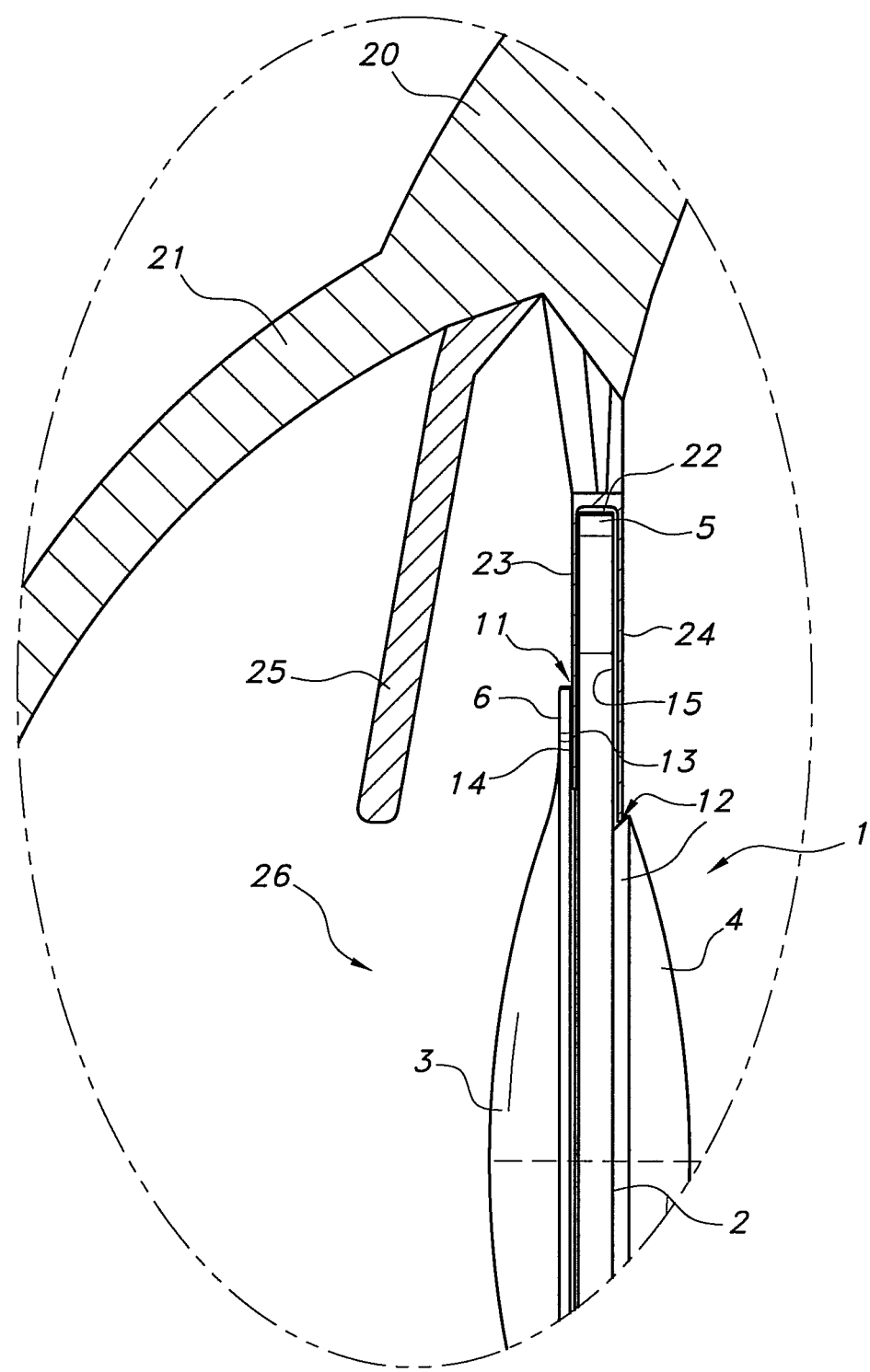
FIG. 10 shows a detail of FIG. 9 as indicated with the IOL of FIG. 1.

In FIG. 10, a detail of FIG. 9 is shown with the IOL 1 of FIG. 1 inserted. The IOL 1 in this example is provided with the posterior groove 12 described earlier.

Here, the posterior capsular bag 24 has the posterior opening explained earlier. The rim of the posterior opening is positioned in the posterior groove 12. The anterior capsular bag flap (a ring of capsular bag membrane material) which remains after an opening is made in the anterior capsular bag part 23 is held between the anterior support 6 and the posterior support 5. The support surface of the anterior support 6 and the support surface of the posterior support 5 both rest against the anterior capsular bag flap, and in fact, although perhaps not indicated that way, may even clamp that flap between them.

Figure 11:
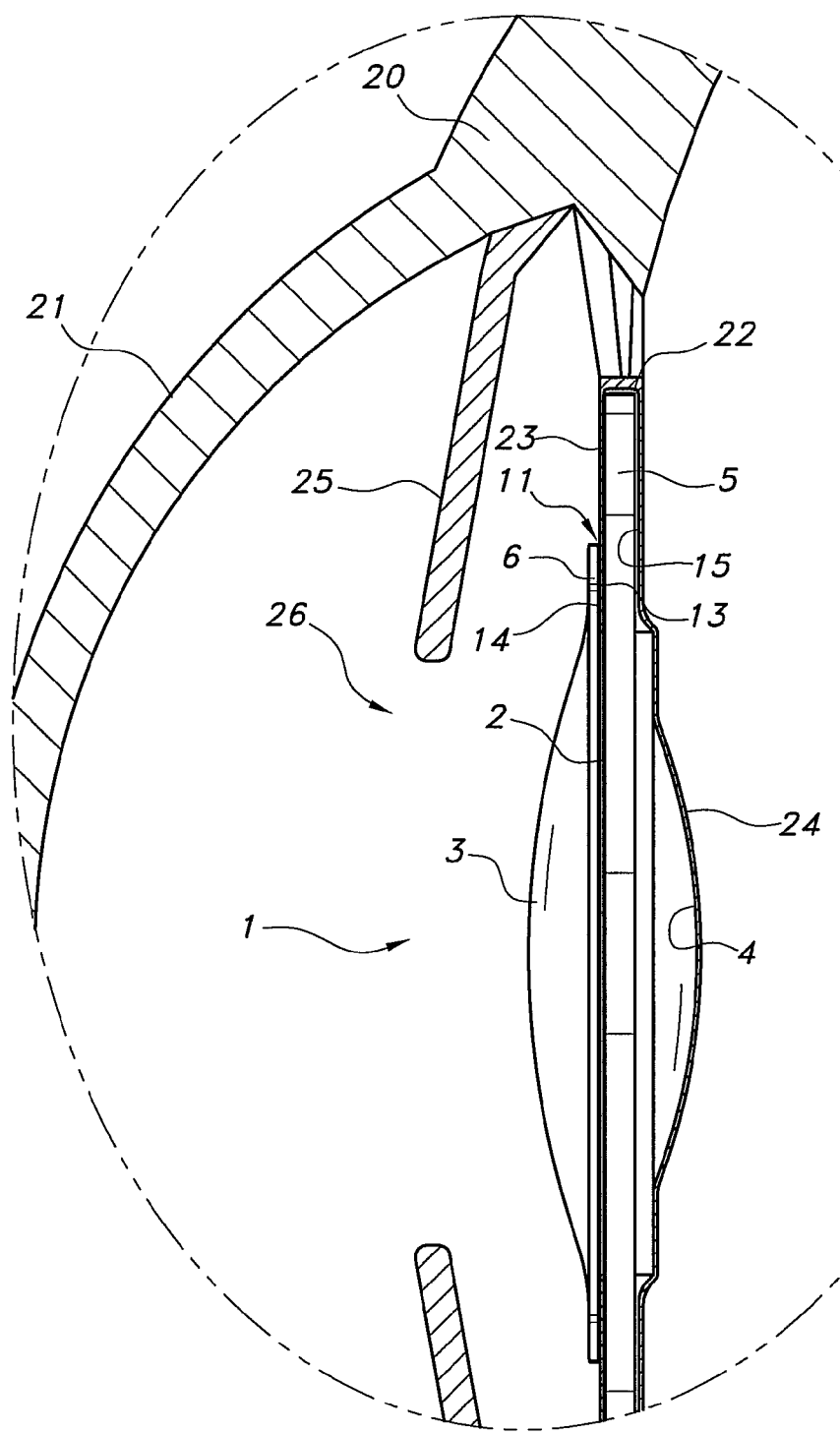
FIG. 11 shows a detail of FIG. 9 as indicated, but with an IOL with an alternative posterior feature and a posterior capsular bag part that is intact.

In FIG. 11, a detail similar to that of FIG. 9 is shown, but with an IOL 1 with an alternative posterior feature. In this case, the posterior capsular bag part 24 does not have an opening: the posterior capsular bag part 24 is in tact and rests against the posterior surface 4 of IOL 1.

In both FIGS. 10 and 11, the posterior supports 5, 5' have a large diameter. The IOL 1, however, is positioned in opening 32 by means of the anterior and posterior supports, possibly combined with mutual fitting of perimeter 7 and the length of the perimeter of opening 32. Thus, the radial dimension of the posterior supports 5, 5' may be reduced.

Insertion of the IOL in an Eye

Insertion of the IOL 1 described so far will be explained below. An example of a procedure of making the incision and implanting the IOL is as such for instance described in U.S. Pat. No. 5,376,115, which is incorporated by reference as if fully set forth. In particular, it describes:

A surgical method gaining in popularity is the phacoemulsification technique, that utilises ultrasonic vibrations to fragment the lens nucleus, thus allowing removal of the lens material through an incision that is approximately 3 mm long. The benefits of a small incision are faster visual rehabilitation, faster healing and less astigmatism than with conventional large incisions. A hollow titanium needle with a diameter of about 1 mm is activated to vibrate by a magnetostrictive ultrasonic mechanism. The mechanical vibrations transform the lens into an emulsion, hence the name phacoemulsification.

As the phacoemulsification technique has been refined the construction of the incision has developed to allow sealing of the wound without the need for sutures—"self sealing incisions".

According to the reference, the technique is described for instance in J Cataract Refract Surg 16(5) (1990) pp. 567-577 by Menapace, R. et al and in Ophthalmology (U.S.) 100(2) (1993) pp. 159-163 by Ormerod, L. D. et al.

U.S. Pat. No. 5,376,115 further describes an example of insertion of an IOL.

This may be combined with the following procedure. Before inserting the IOL 1 into the capsular bag, first an opening is made in the anterior part of the capsular bag. Using for instance a laser device like the Femto laser, an opening or aperture can be made in the anterior membrane or anterior capsule of the capsular bag that has a precise shape and precise position. This procedure is also referred to as 'Capsularhexis', although recent literature refers to a laser-based procedure as 'Capsulotomy', and uses that term in contrast to 'Capsularhexis', which term is then used to refer to mechanically tearing or cutting an opening in the capsular bag. Other laser-based procedures are currently also developing. In these procedures, a laser beam is directed through the cornea and into the eye, where its energy is absorbed in an internal structure in order to cut that structure. In one of these procedures, the anterior capsular bag membrane is coloured with a light-absorbing agent. The absorption properties of that light-absorbing agent are selected in order to absorb the laser beam energy.

In many cases, for instance in case of a cataract, in a next step the cloudy natural lens is removed through the opening in the capsular bag. In this step, the natural lens can be treated with a laser first, before it is removed, for instance with a phaco emulsification device. Removal of the natural lens as such is known to skilled person.

In an optional next step, a posterior opening can be made in the posterior part of the capsular bag, in the posterior membrane or posterior capsule of the capsular bag.

An example of such a classic Capsularhexis procedure and the use of a laser device in such a procedure is described in U.S. Pat. No. 8,409,182, which is incorporated herein by reference as if fully set forth. For instance in column 3, an example of steps in a Capsularhexis procedure or, more specific, a capsulotomy procedure, is described. The laser-assisted procedure allows accurate positioning as well as shaping of the opening. Furthermore, such a procedure can leave a relatively strong edge around the created opening in the capsular bag. In particular, regarding a laser-based procedure the following was found.

METHODS: Capsulotomies performed by an optical coherence tomography-guided femtosecond laser were evaluated in porcine and human cadaver eyes. Subsequently, the procedure was performed in 39 patients as part of a prospective randomized study of femtosecond laser-assisted cataract surgery. The accuracy of the capsulotomy size, shape, and centration were quantified and capsulotomy strength was assessed in the porcine eyes.

RESULTS: Laser-created capsulotomies were significantly more precise in size and shape than manually created capsulorhexes. In the patient eyes, the deviation from the intended diameter of the resected capsule disk was 29 µm±26 (SD) for the laser technique and 337±258 µm for the manual technique. The mean deviation from circularity was 6% and 20%, respectively. The centre of the laser capsulotomies was within 77±47 µm of the intended position. All capsulotomies were complete, with no radial nicks or tears. The strength of laser capsulotomies (porcine subgroup) decreased with increasing pulse energy: 152±21 mN for 3 mJ, 121±16 mN for 6 mJ, and 113±23 mN for 10 mJ. The strength of the manual capsulorhexes was 65±21 mN.

CONCLUSION: The femtosecond laser produced capsulotomies that were more precise, accurate, reproducible, and stronger than those created with the conventional manual technique.

Source: J. Cataract Refract. Surg. 2011; 37:1189-1198 Q 2011 ASCRS and ESCRS.

Test further showed the following results.

METHODS: Ten fresh pig eyes were randomly assigned to femtosecond laser-assisted capsulotomy or manual capsulotomy. The capsule was immersed in hyaluronic acid, and retractors were fixed in the capsule opening with a pull-force measuring device. The force necessary to break the capsulotomy was measured in millinewtons (mN); the maximum stretching ratio was also assessed.

RESULTS: The observed mean rupture force (i.e., maximum amount of force measured immediately before tissue rupture) was 113 mN±12 (SD) in the laser-assisted procedure and 73±22 mN in the manual procedure (P<0.05). The stretching ratios were 1.60±0.10 (femtosecond) and 1.35±0.04 (manual) (P<0.05).

CONCLUSION: In this laboratory pig-eye study, femtosecond laser-assisted capsulotomy resulted in a significantly stronger anterior capsule opening than the standard manually performed capsulotomy.

Source: J. Cataract Refract. Surg. 2013; 39:105-109 Q 2013 ASCRS and ESCRS.

A very accurate positioning of an opening 32 in a capsular bag 22, and a very accurately shape of the opening 32, allows an accurate positioning and orientation of the IOL 1 described, and is in particular advantageous when using the current IOL or IOL/S-IOL combination.

The IOL 1 can be used in the following way. Often, the IOL 1 is inserted in the capsular bag via a micro incision in the eye. Via an insertion device, the IOL outside the eye is rolled up and urged forward through a nozzle that fits through the incision in the eye. The rolled-up IOL 1 enters the capsular bag via the opening. The rolled-up IOL 1 unfolds inside the capsular bag.

Next, using a small tool, the anterior supports 6, 6' are manipulated to fold back through the opening 32 in the anterior capsular bag part 23 to extend outside the capsular bag 22. Using the same or an identical tool, the lips 8, 8' may be manipulated to also extend through the opening 32 and to reach out of the capsular bar 22. The posterior surfaces 17 and 17' of the lips 8, 8' will then rest on the anterior surface of the anterior part 23 of the capsular bag 22. If the posterior capsule is opened as well then in a second manoeuvre by gently pushing the IOL a little bit downward the posterior flap will be secured in the posterior groove 12.

The Intraocular Lens Assembly and the Secondary Intraocular Lens (S-IOL)

In the next FIGS. 12-35 and 40-46, some embodiments of the intraocular lens assembly and the secondary intraocular lens (S-IOL) will be described. The various features can be combined. In FIGS. 12-27, a first embodiment of the intraocular lens assembly will be described that is based on the IOL 1 that is described separately in FIGS. 1-7B. In FIGS. 28-35, a second embodiment of the intraocular lens assembly is based on the IOL 1 that is described separately in FIG. 8. It should be noted, as mentioned before, that the rear feature of the posterior rim 16 and the posterior groove 12 can both be used in these designs, and may even be combined. The embodiments shown here use the posterior rim 16.

Figure 12:
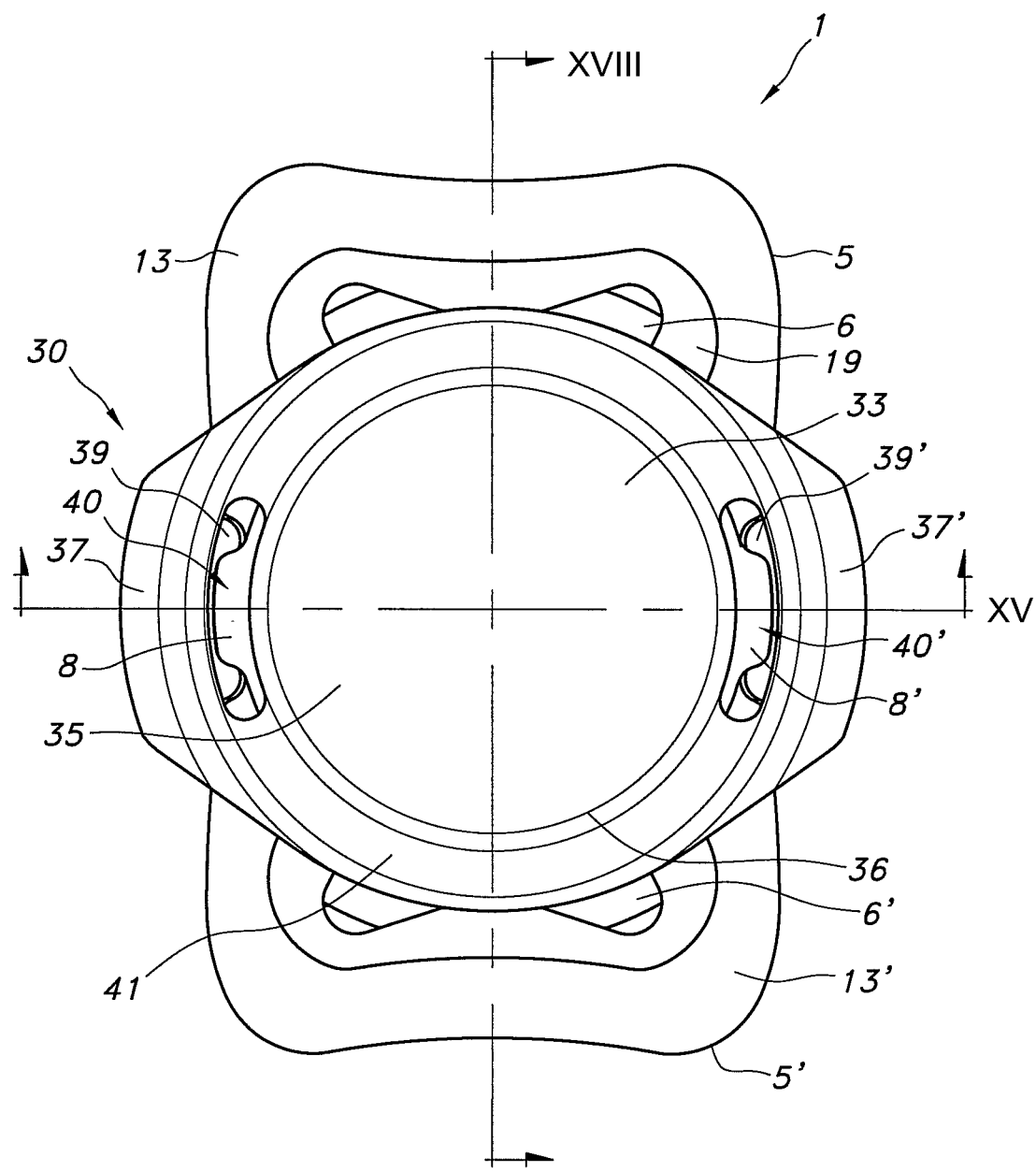
FIG. 12 shows a front view of the IOL of FIGS. 4 and 5 with a secondary intraocular lens (S-IOL) attached to it.
Figure 13:
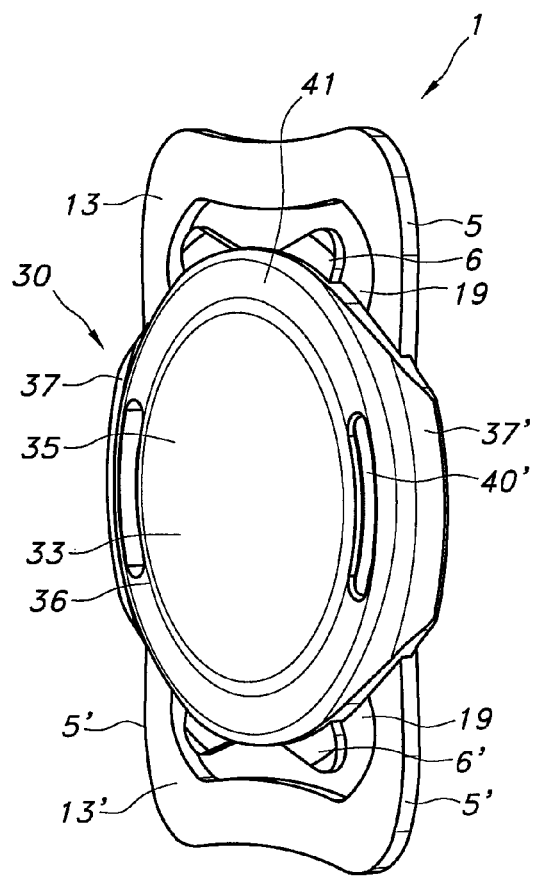
FIGS. 13 and 14 show a perspective view of FIG. 12 in anterior and posterior view.
Figure 14:
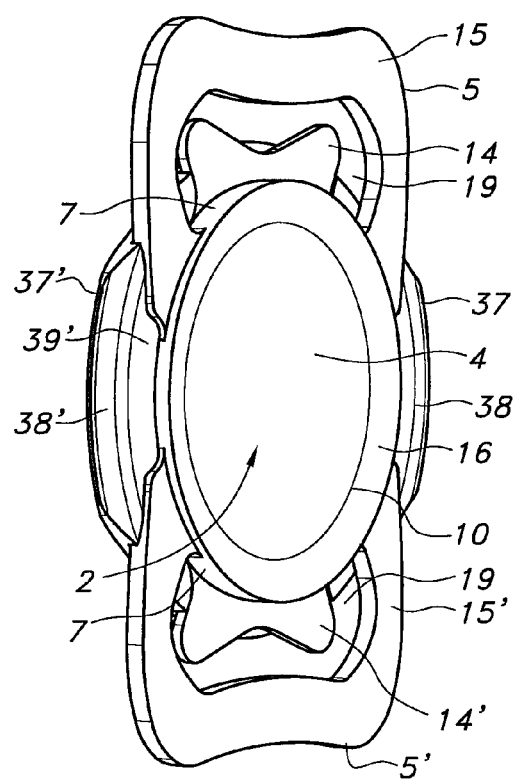
Figure 15:
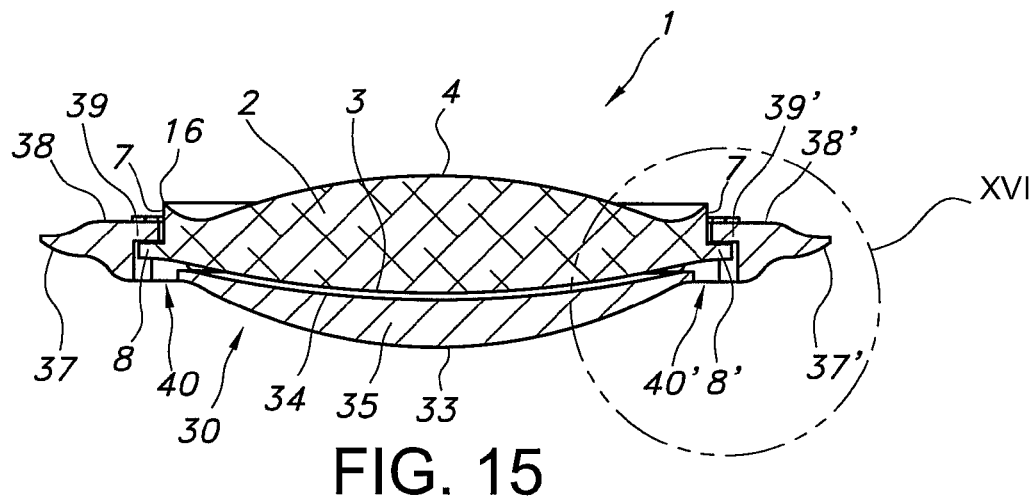
FIG. 15 shows a cross section of FIG. 12 as indicated in FIG. 12.
Figure 16:
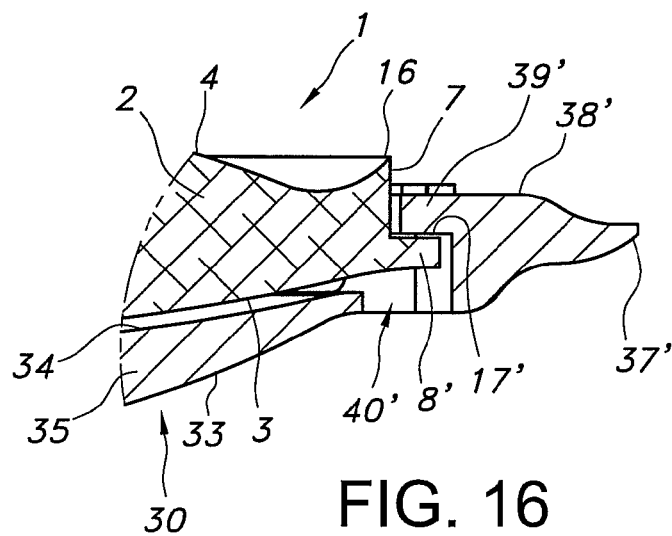
FIG. 16 shows a detail of FIG. 15 as indicated.
Figure 19:
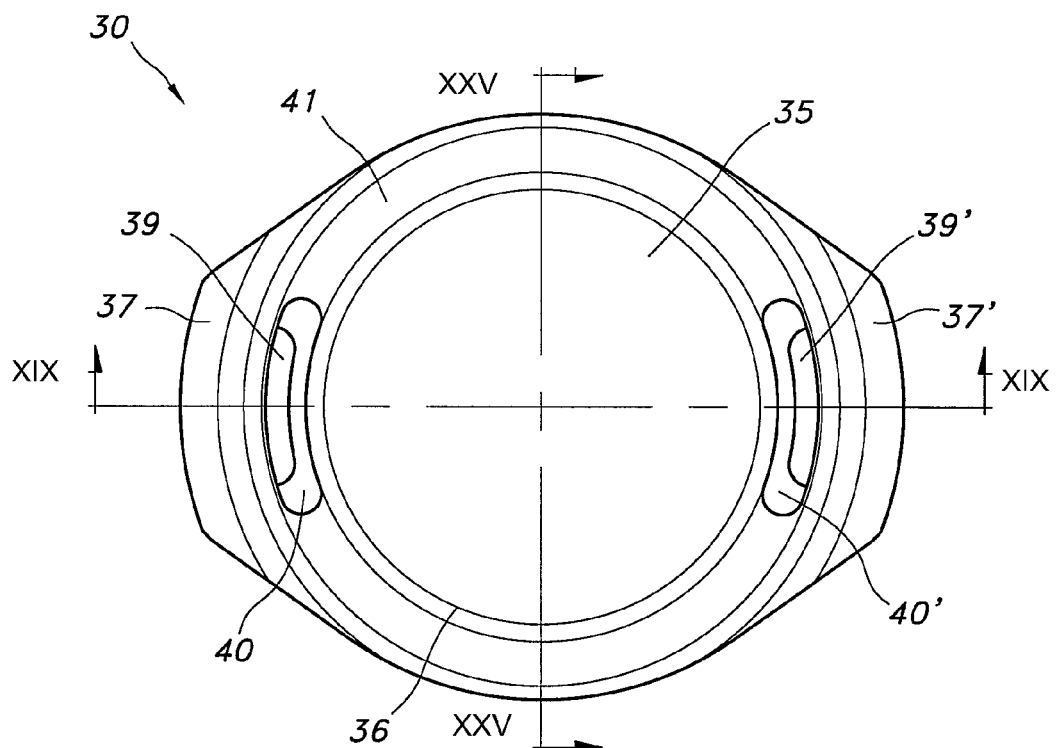
FIG. 19 shows the S-IOL of FIG. 12 from its anterior (front) side.
Figure 20:
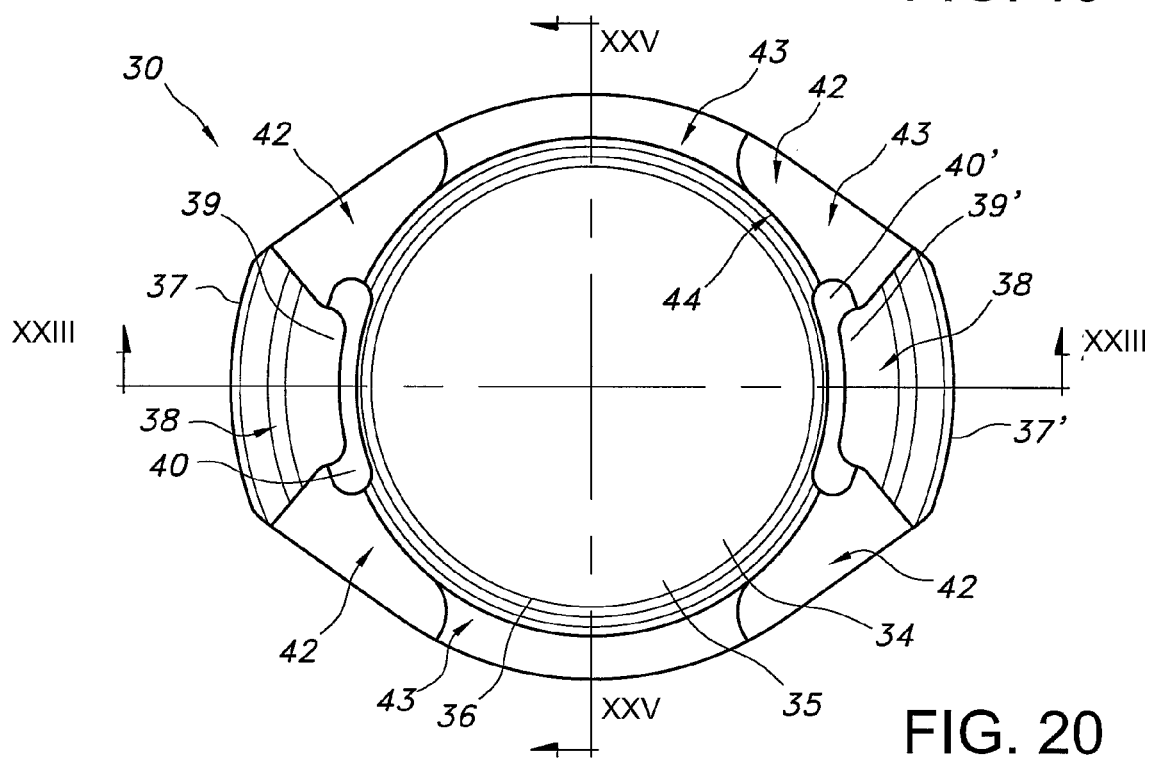
FIG. 20 shows the S-IOL of FIG. 12 from its posterior (rear) side.
Figure 21:
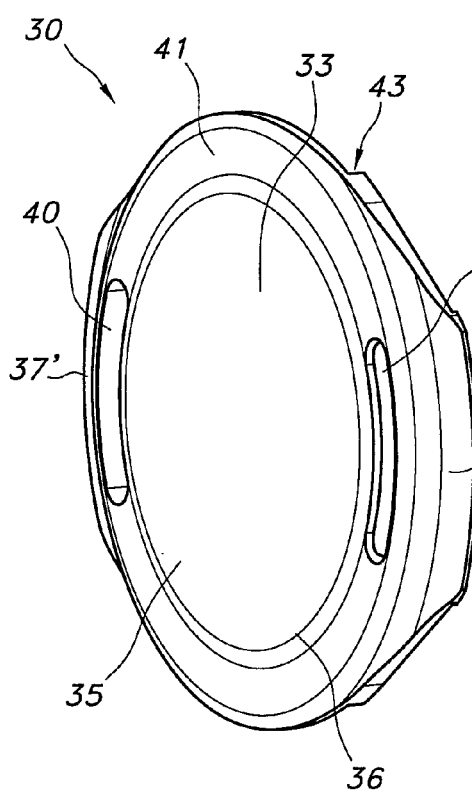
FIGS. 21 and 22 show a perspective view of the S-IOL of FIG. 19 in anterior and posterior view, respectively.
Figure 22:
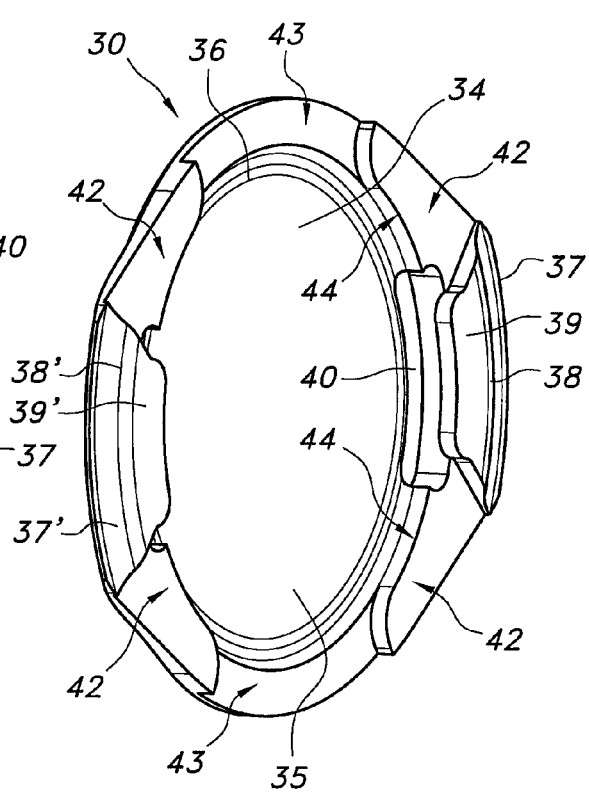
Figure 23:
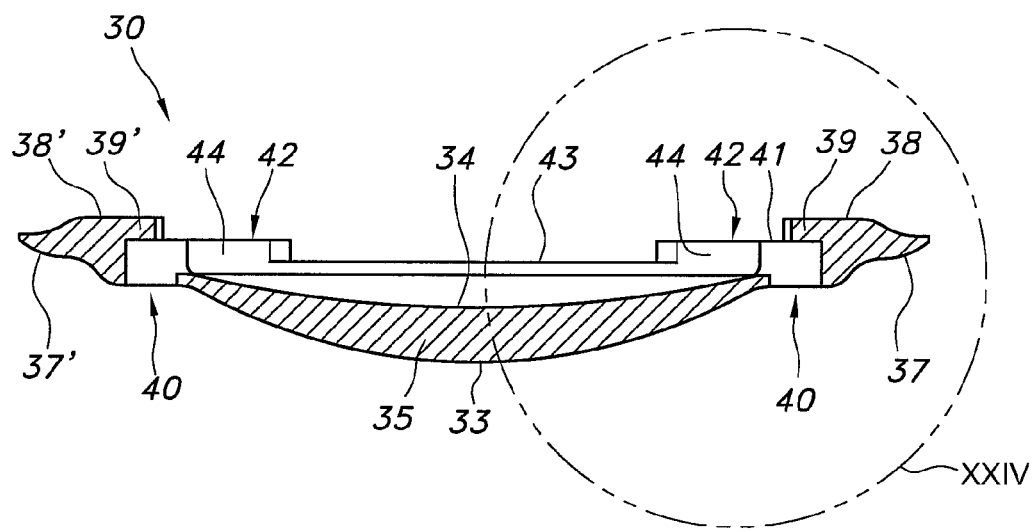
FIG. 23 shows a cross section of FIG. 19 as indicated.
Figure 24:
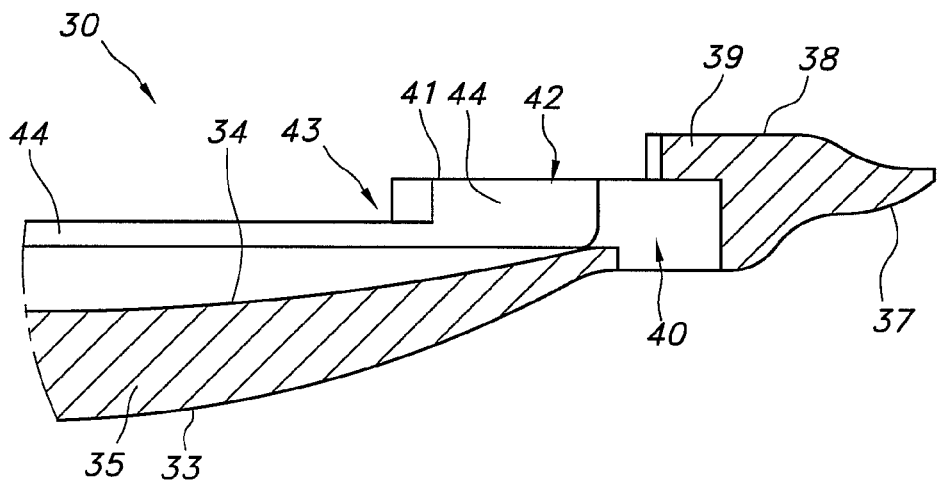
FIG. 24 shows a detail of FIG. 23 as indicated.
Figure 25:
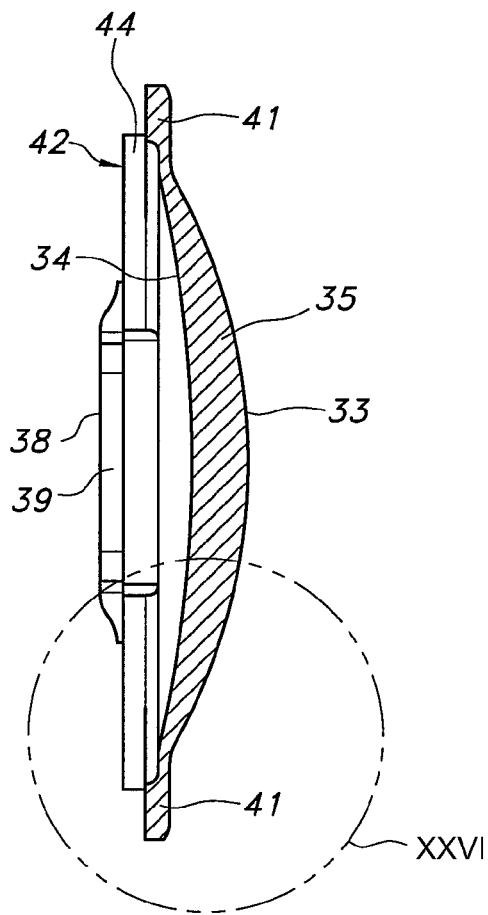
FIG. 25 shows a cross section of FIG. 20 as indicated.
Figure 26:
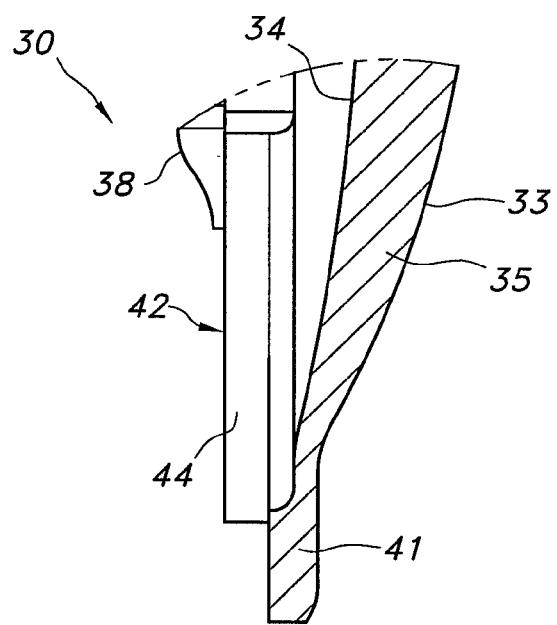
FIG. 26 shows a detail of FIG. 25 as indicated.
Figure 30:
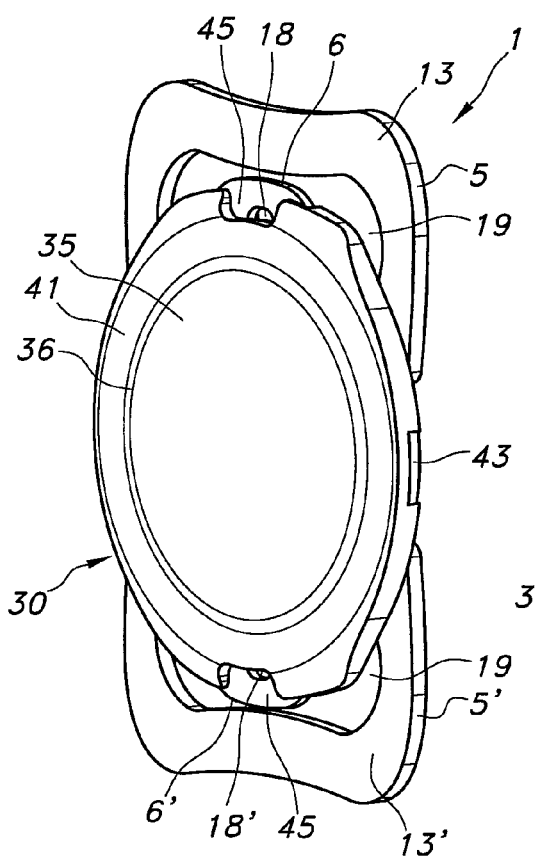
FIGS. 30 and 31 show a perspective view of the S-IOL of FIG. 28 in anterior and posterior view, respectively.
Figure 31:
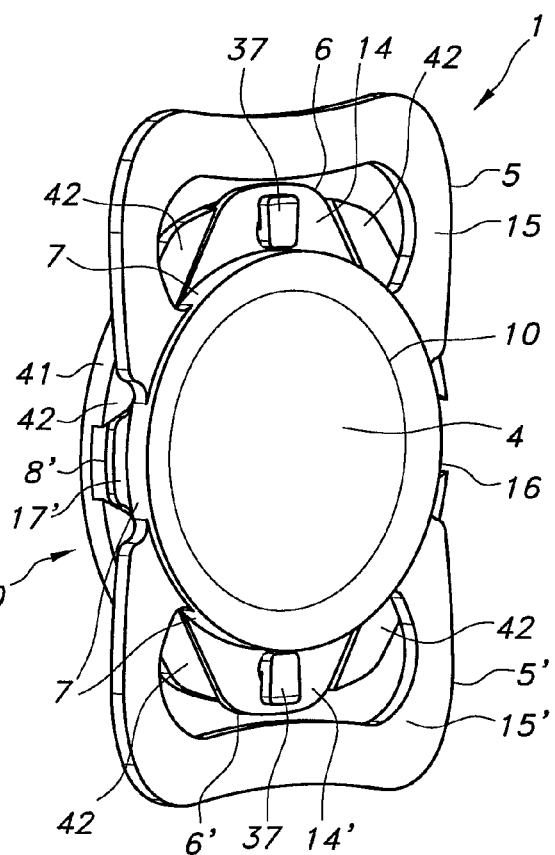
Figure 32:
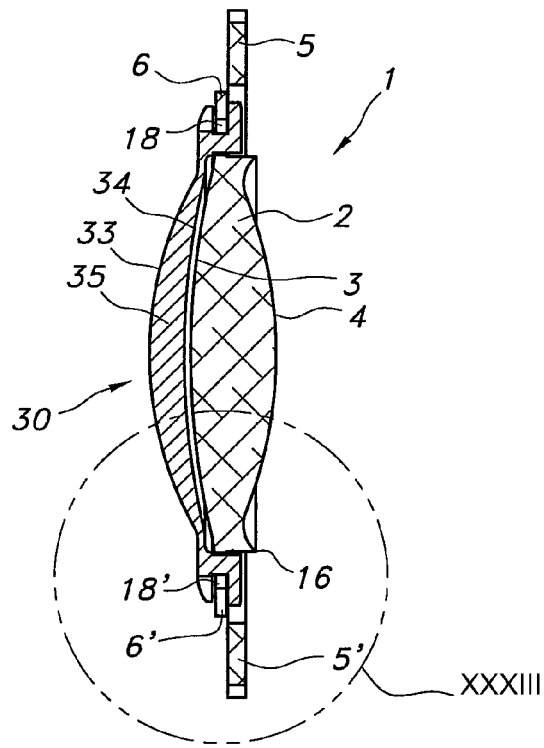
FIG. 32 shows a cross sectional view of the assembly of FIG. 28 as indicated in that FIG. 28.
Figure 33:
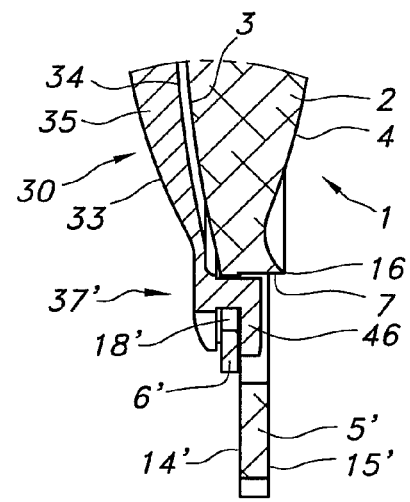
FIG. 33 shows a detail of FIG. 32 as indicated.
Figure 34:
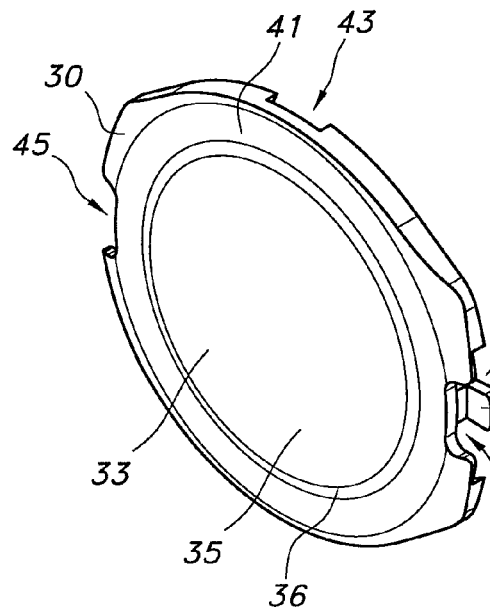
FIGS. 34 and 35 show a perspective view of the alternative S-IOL of FIG. 28 in anterior and posterior view, respectively.
Figure 35:
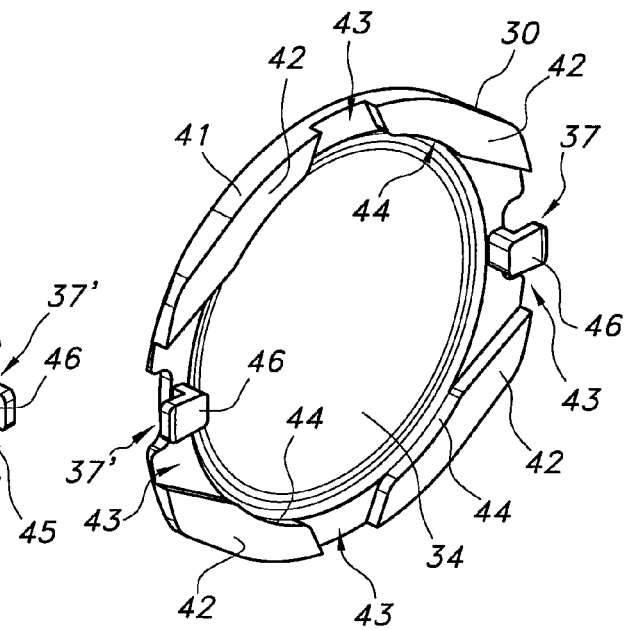

In FIGS. 12-18, several views are shown of the intraocular lens assembly comprising the IOL 1 and a secondary intraocular lens (S-IOL) 30. FIG. 12 shows a view from the anterior side, FIGS. 13 and 14 show a perspective view from respectively the anterior side and the posterior side, and FIGS. 15-18 show various cross sections and details. In FIGS. 19-26, some details of the S-IOL 30 of the first embodiment are shown.

The S-IOL 30 has an anterior surface 33 and a posterior surface 34. Posterior surface 34 of the S-IOL 30 faces the anterior surface of the IOL 1. The S-IOL 30 has a secondary optical structure 35. Such an optical structure 35 may be a simple lens having a spherical positive or negative dioptre. Often, the spherical dioptre is between −8.0 and +8.0. Alternatively or additionally, the optical structure 35 may also comprise a near part ('reading part'), astigmatic optics, torical optics, and combinations thereof. Furthermore, multifocal optics as described in WO2012/118371 can also be used. Also other active or passive optics known to a skilled person may be used. The secondary optical structure 35 has a secondary perimeter 36. Coupled to the secondary perimeter 36 are fixing parts 37, 37'.

At their posterior side 38, 38', the fixing parts 37, 37' have lips 39, 39'. Lips 39, 39' extend in inward direction with respect to the perimeter. The lips 39, 39' are thus spaced from the posterior surface 34 of the secondary optical structure 35. In this embodiment, the fixing parts 37, 37' are adapted to reach about anterior supports or anterior lips 8, 8'. In this way, the parts of the lips 39, 39' are located at the posterior sides of anterior supports 8, 8'. They are thus at least partly positioned between the anterior support 8, 8' and the capsular bag 22. The elasticity of the capsular bag urges the lips 39, 39' against the anterior supports 8, 8'. This helps in fixation. Furthermore, as the parts are pushed together, it is possible to further fix them together through cohesion if similar materials are used. The thickness of the lips 39, 39' is between 0.1 and 0.4 mm, more in particular between 0.15 and 0.25 mm.

In this embodiment of the assembly, the fixing parts 37, 37' thus hook behind anterior supports, here the anterior supports 8, 8' that are also referred to as anterior lips 8, 8'. The fixing parts 37, 37' in this embodiment thus provide hooks. These hooks have ends that extend at the posterior surface of the anterior supports, here anterior supports 8, 8'. Furthermore, in this embodiment the fixing parts 37, 37' provide hooks that hook about radial ends of the anterior supports 8, 8'.

The S-IOL further comprises openings 40, 40' outside the perimeter 36 of the secondary optical structure 35. These openings 40, 40' are furthermore azimuthally positioned at the locations of the fixing parts 37, 37'. Through the openings, the lips 39, 39' of the fixing parts 37, 37' are visible when viewing the S-IOL from its anterior side. In azimuthal sense, the openings 40, 40' extend beyond the azimuthal width of the lips 39, 39'. This makes production of the S-IOL for instance by tooling or moulding possible. Furthermore, it allows visual inspection of the positioning of the fixing parts 37, 37' hooking behind the anterior supports 8, 8'. Openings 40, 40' can be about 0.7×2.5 mm. Openings 40, 40' furthermore allow exchange of liquids between parts of the eye and/or of the liquid between the IOL 1 and the S-IOL 30.

In this embodiment, the S-IOL 30 further comprises a ring 41 about the perimeter 36 of the secondary optical structure 35. The ring 41 is here attached to the optical structure. In fact, the ring 41 is here formed together with the secondary optical structure 35 as one part. Here, the fixing parts 37, 37' are in turn attached to the perimeter of the ring 41. If the secondary optical structure 35 is circular, the ring 41 often also is circular.

Ring 41 of S-IOL 30 in this embodiment provides (additional) axial and radial positioning of the S-IOL 30 on the IOL 1, as well as support for the secondary optical structure 35. Ring 41 provides a posterior ring surface 42 for engaging the anterior surface of the capsular bag flap 23 adjacent the opening 32 in the capsular bag 22. In fact, in an embodiment, the ring 41 can be dimensioned to match the opening 32 in the capsular bag 22. For instance, the inner diameter of the ring 41 can have at least the diameter of the opening 32. In an embodiment, the inner perimeter of ring 41 has a diameter to at least fit around opening 32. The posterior ring surface 42 can be adapted to the surface of the capsular bag. Thus, usually, the posterior ring surface 42 is in a plane, in particular a flat plane. In particular, posterior ring surface 42 has a height of 0.05-0.5 mm. Thus posterior ring surface 42 provides axial positioning.

The inner diameter of ring 41 in another or combined embodiment matches the diameter of the perimeter 7 of the optical structure of the IOL 1. The ring 41 fits around the perimeter 7. In an embodiment, ring 41 fits around perimeter 7. Inner peripheral surface 44 of ring 41 thus provides radial positioning of the S-IOL 30 on the IOL 1. In the embodiment shown, the shape of the ring 41 of the S-IOL 30 is adapted to the perimeter 7 of the IOL 1. Often, the inner peripheral ring surface 44 is cylindrical. If the ring 41 is circular, the inner ring surface 44 may be circle cylindrical. In such an embodiment, the inner ring surface 44 may engage perimeter 7 of the IOL 1, which can be seen in FIGS. 14 and 31. Thus, radial positioning is provided.

In order to provide easier application, the inner peripheral surface 44 can be conical, or tapered, and the perimeter of the IOL 1 can be conical or taper correspondingly. Thus, bringing the S-IOL 30 on the IOL 1 can be easier, and once fitted, the surface of the perimeter 7 and the inner peripheral ring surface engage.

In order to fit the S-IOL 30 onto the IOL 1 better, the ring 41 can be provided with recesses or cut-outs 43 for allowing the anterior and/or posterior supports to pass the ring 41. In an embodiment, the cut-outs 43 are shaped such that a cut-out 43 matches the shape of the supports that passes that cut-out 43. Thus, further fixation is possible, and even fixing through local cohesion between the IOL 1 and the S-IOL 30 where surfaces of the IOL 1 and the S-IOL 30 are in contact. In particular if the materials of the IOL 1 and the S-IOL 30 are of a similar nature, it was found that parts of the IOL 1 and the S-IOL 30 that are in contact with one another stick onto one another. With similar nature in this respect is meant that for instance the polymers used are of the same type. For instance, both the IOL 1 and the S-IOL 30 are made from either hydrophilic or hydrophobic polymers selected from acrylate-based polymers, silicon-based polymers, of other known materials. In these materials, the hardness may differ.

Ring 41 furthermore can provide a spacing between the posterior surface 34 of the secondary optical structure 35 and the anterior surface 3 of the optical structure 2. The distance can be 0.05-0.2 mm. In particular, the spacing can be 0.05-0.15 mm. The spacing allows formation of a liquid film that can act as an additional lens, often adding −2 to +2 Dioptre.

The radial ends of fixing parts 37, 37' are rounded in order to prevent interference with the iris.

In use, after the IOL 1 is inserted, positioned and fixed as described above, usually some time later the refractive error of the person that received the IOL 1 will be determined. Based upon the measured values, an S-IOL 30 will be selected from a set of S-IOL's that has an optical structure 35 that will for instance correct any remaining optical imperfections as much as possible, or it may provide for instance a reading part. Alternatively, such an S-IOL can be custom made. Using the previous incision that was also used for inserting the IOL1, the S-IOL 30 can be inserted in the eye. Thus, no new refractive errors due to incisions will be introduced. Using the openings 40, 40' the S-IOL 30 can be manipulated and positioned with its posterior surface 34 facing the anterior side 3 of the IOL 1. Next, the fixing parts 37, 37' will be fitted about the ends of anterior supports 8, 8'. The posterior surfaces of the fixing parts 37, 37' are pushed tightly against the anterior surface of the capsular bag and deform it. In FIG. 27, this is clearly indicated in the cross section through a lip 39 and anterior support 8. The elasticity of the capsular bag assists in fixing the intra ocular lens assembly. Furthermore, in an embodiment the posterior ring surface 42 pushes against the capsular bag surface. From inside the capsular bag 22, posterior support pushes against the capsular bag. This provides additional clamping of the capsular bag.

In FIGS. 28-35, a second embodiment of the intraocular lens assembly is shown. This assembly comprises the IOL 1 described in FIG. 8. In this embodiment, the anterior supports 6, 6' comprise support openings or through holes 18, 18'. In this embodiment, the S-IOL 30 comprises fixing parts 37, 37' that reach through the openings 18, 18' through the anterior supports 6, 6'. At their ends, the fixing parts 37, 37' each have a locking part 46 extending to the posterior surface 14, 14' of the anterior supports 6, 6'. In FIG. 29, the view on the posterior side, it can be seen how the locking parts 46 extend to the posterior surface 14, 14' of the anterior supports 6, 6'. When the intra ocular lens assembly is in use and placed in the opening and fixed to the capsular bag flap 23, the relatively elastic tissue of the capsular bag 22 will push against both the posterior surfaces 14, 14' of the anterior supports 6, 6' and pushes the locking parts 46 in anterior direction against that posterior surfaces 14, 14' of the anterior supports 6, 6', thus further blocking the fixing parts 37, 37 from getting back through openings 18, 18'. A further advantage of the fixing parts 37, 37' that reach through openings 18, 18' in the anterior supports 6, 6' is that rotation of the S-IOL 30 is blocked. The S-IOL 30 is thus fixed to the IOL 1 in axial (Ax), radial (Ra), and azimuthal (Az) sense.

Using the laser-assisted procedure, it is further possible to produce through holes in the anterior capsular bag part 23 at a small distance from the edge of opening 32. In particular, these small through holes (additional capsulotomies) can be produced at the locations of openings 18, 18' in the anterior supports 6, 6'. The fixing parts 37, 37 in this case may also reach through these through holes in the anterior capsular bag 23 to provide additional clamping and securing. Alternatively or additionally, further fixing means on the S-IOL may be provided that reach through these through holes in the anterior capsular bag part 23.

The S-IOL 30 in this embodiment further again comprises a ring 41 about the perimeter 36 of the optical structure 35. This ring 41 has the same features described above, but in some instances designed differently. The fixing parts 37, 37' are in this embodiment attached to the posterior ring surface 42 of ring 41. In particular, fixing parts 37, 37' here extend from that surface. The ends of the fixing parts 37, 37' are provided with patches 46 that provide surfaces that are here in plane with the posterior ring surface 42, but these surfaces may extend further in posterior direction/posterior sense/axial sense. The patches may be sized to fit the openings or holes 18, 18' in the anterior supports 6, 6' they should pass when positioning and fixing the S-IOL 30 on the IOL 1. There, the fixing parts 37, 37' are located in cut-outs 43 for the anterior supports 6, 6'. Thus, the further posterior ring surface 42 in use can rest or even press against the capsular bag as explained. Due to the cut-outs or recesses 43, the posterior ring surface 42 is divided into separate areas. Usually, these areas are in one plane to be able to engage the capsular bag surface. The depth of cut-outs or recesses 43 is adapted that the surface of the recesses or cut-outs 43 engages the anterior surfaces of the anterior supports 6, 6', 8, 8'.

The S-IOL 30 further comprises cut-outs 45 in its perimeter at the fixing parts 37, 37'. Thus, the ends of fixing parts 37, 37', in particular the patches 46, are visible when the S-IOL is viewed from the anterior side. Thus, the person inserting and placing the S-IOL can see these parts and the relevant part of the IOL 1 during fixing of the S-IOL 30 to the IOL 1.

The various parts of the posterior side of the S-IOL 30 and of the anterior part of the IOL 1 are mutually shaped to engage one another over an area of surface. In case the S-IOL 30 and the IOL 1 are of the same or identical material, in particular polymer material that is flexible and foldable, and have a smooth surface, it was found that cohesion occurs. In fact, it was found that after some time, the material of the S-IOL 30 and the IOL 1 stick together and must be peeled off one another with some effort. Thus, the various surfaces that are discussed can be designed and arranged such that the IOL 1 and the S-IOL 30 remain attached to one another after both elements of the assembly are in place.

In an embodiment, the various parts of the IOL 1 and the S-IOL 30 are mutually dimensioned to result in a distance between the anterior surface 3 of the optical structure 2 of the IOL 1 and the posterior surface 34 of the secondary optical structure 35 of the S-IOL 30. Thus, the anterior surface 3 of the optical structure 2 of the IOL 1 remains free from the posterior surface 34 of the secondary optical structure 35 of the S-IOL 30. The distance can be between 0.03-0.5 mm, in particular 0.05-0.25 mm. Thus, a film of anterior chamber liquid may form between the IOL 1 and the S-IOL 30. In an optical sense, such a film of liquid can have an effect of −2 to +2 dioptre, in particular −0.5 to +0.5 dioptre (in case of a spherical film causing a spherical lens). In an embodiment, the anterior surface of the IOL 1 of the optical structure 2 and the posterior surface of the optical structure of the S-IOL 30 have a radius of curvature that is substantially the same, making a design of the assembly in which an IOL can be combined with a selection of S-IOLs easier as the film of liquid will be the same. For both surfaces, the radius of curvature can be for instance between 9 and 13 mm. Matching the radius of curvature may result in a reduction of the number of S-IOLs that need to be kept in stock.

Implanting the S-IOL

Implanting the S-IOL is relatively simple. Using the previous incision that was also used for inserting the IOL 1, the S-IOL 30 can be inserted in the eye. Thus, no new refractive errors will be introduced. The S-IOL 30 is placed in axial sense between the iris and the IOL 1 via the already existing micro incision in the eye. Via an insertion device, the S-IOL 30 outside the eye is rolled up and urged forward through a nozzle that fits through the incision in the eye. The rolled-up S-IOL 30 enters the eye via the iris. The rolled-up S-IOL 30 unfolds in front of the IOL 1. Using for instance the openings 40, 40', the S-IOL 30 can now be manipulated and positioned with its posterior surface 34 facing the anterior side 3 of the IOL 1. Next, the fixing parts 37, 37' will be fitted about the ends of anterior supports 8, 8'. Alternatively, the fixing parts 37, 37' can be fitted through the openings 18, 18' in the anterior supports 6, 6'. The posterior surfaces of the fixing parts 37, 37' are pushed tightly against the anterior surface of the capsular bag and deform it. The flexibility and elasticity of the capsular bag membrane is additionally used to hold the S-IOL in place.

Figure 37:
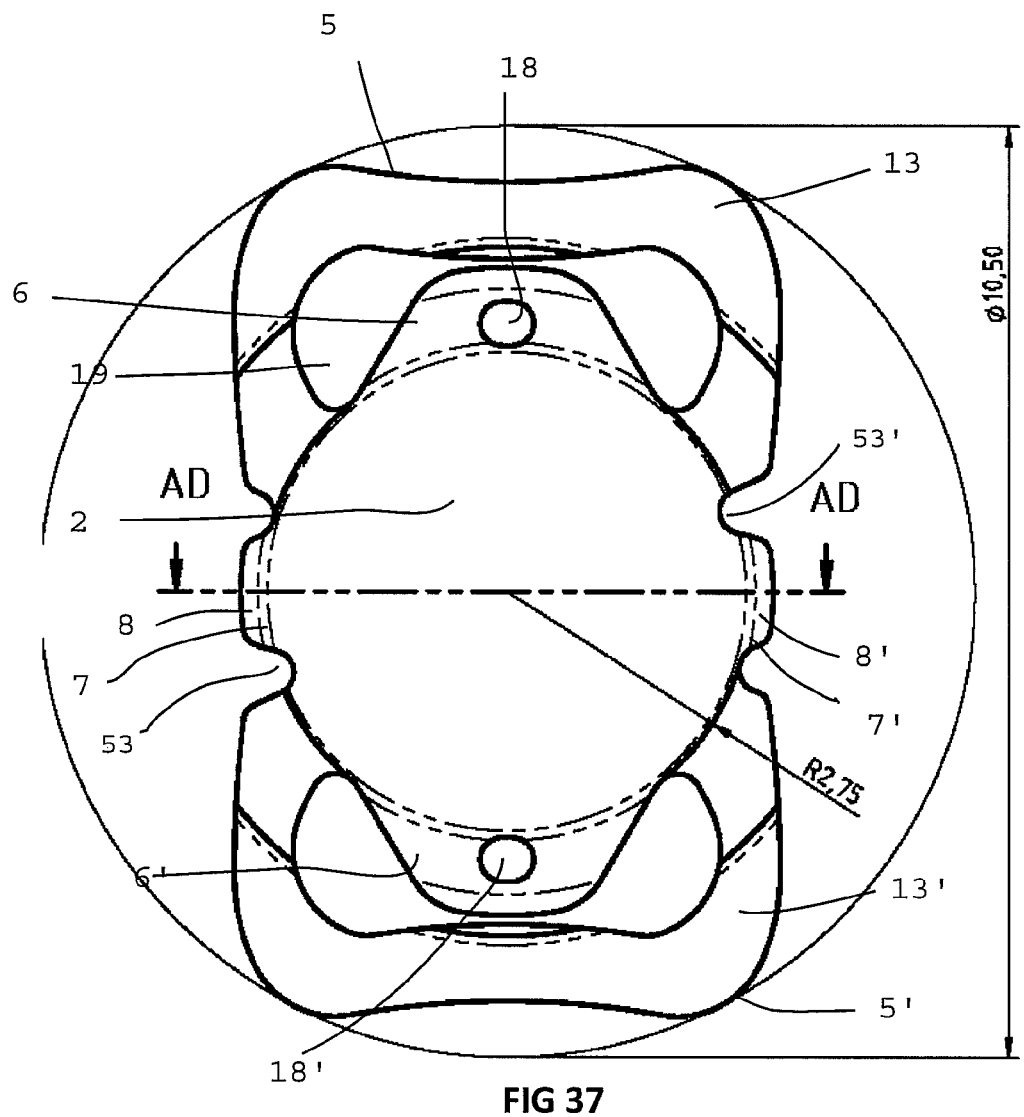
FIGS. 37 and 38 an alternative embodiment of the IOL of FIG. 8, in front view and in perspective partly from the rear.
Figure 38:
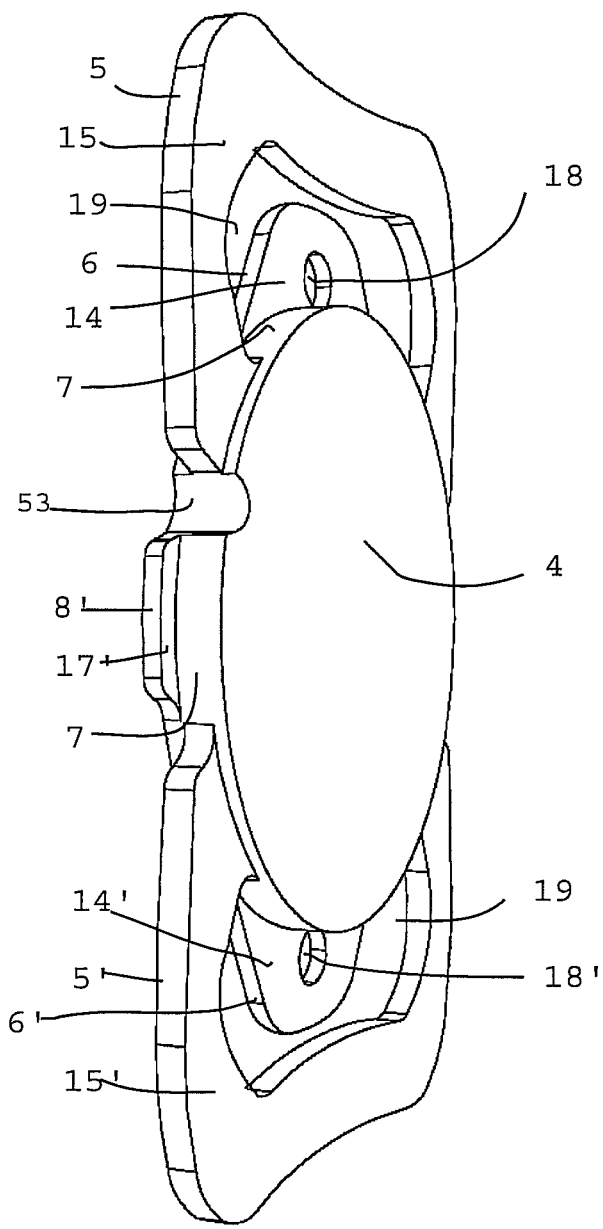

In FIGS. 37 and 38, an alternative embodiment of the IOL 1 of FIG. 8 is shown. In FIG. 38, the embodiment of FIG. 37 is shown partly from the rear in perspective. Again, similar reference numbers show similar elements.

Capsular bag distension syndrome (CBDS) is an uncommon, but well recognized cause of reduced vision following cataract surgery. It usually presents in the immediate postoperative period, with shallowing of the anterior chamber, unexpected myopic refraction and accumulation of liquefied substance between the implanted lens and posterior capsule.

The most likely mechanism of CBDS is the production of collagens from residual lens epithelial cells or necrotic and/or apoptotic autolyzed lens epithelial cells or the retained viscoelastic from the surgical procedure accumulates behind the intraocular lens (IOL) as the IOL optic occludes the anterior capsular opening made by the capsulotomy. The creation of a small opening in the lens to avoid total sealing of the bag may avoid this post-operative complication. The opening could be shaped in the form of notch at the optic edge or a small hole made in the optic. It is also possible to create small capsulotomies when the capsule opening is made in the anterior or posterior capsule flaps to avoid complete sealing of the capsular opening when using the IOL described earlier.

In the embodiment of FIG. 37 an 38, another approach is chosen. In this embodiment, an indentation 53 is created in the peripheral surface 7. This indentation 53 provides an axial (Ax) groove in the perimeter 7 about the IOL. Here, the groove as straight in axial (Ax) direction, but amendments may be made to control flow of fluid. This creates a passage between the peripheral surface 7 and the edge of the opening 32 in the anterior part of the capsular bag 23 after insertion of the IOL 1. Thus, a passage for fluid is provided once the IOL is inserted in the opening 32 in the capsular bag. In fact, even if the posterior groove 12 is provided in the IOL, this groove may provide a passage for fluid part once the posterior part of the capsular bag is inserted in the posterior groove 12. In fact, the radial extension of the indentation may control such a passage.

In order to provide an easy passage, the indentation 53 is provided in radial sense next to a posterior support 5, 5' or an anterior support 6, 6'. In the embodiment shown in the drawings, the indentation 53 is provided between a posterior support 5, 5' and an anterior support 6, 6'. In this embodiment, two indentations 53, 53' are provided, here opposite one another. Here, the diameter of the indentations 53, 53' are selected to allow eye fluid to pass the passage. In this embodiment, the width of the indentations 53, 53' is here 0.2-0.6 mm. In particular, the width is 0.25-0.5 mm. The depth of the indentations 53, 53' is here 0.05-0.4 mm. In particular, the depth is 0.1-0.3 mm.

In an embodiment, the S-IOL 30 comprises a through channel or indentation, providing a passages for fluid and connecting to the indentation. In this way, a passage for fluid remains once the IOL 1 is placed in the capsular bag and the S-IOL 30 is positioned on the IOL 1. The S-IOL may comprise a through hole at or near its outer rim and connecting to the indentation when the S-IOL 30 is placed in the IOL 1. The fluid passage may allow fluid to flow between the anterior side of the capsular bag and the inside of the capsular bag. It may also allow fluid exchange to the posterior side of the capsular bag. The hole or channel may be provided through the ring 41 of the S-IOL 30. The accurate mutual positioning of the IOL 1 and the S-IOL 30 with respect to one another insures a proper fluid passage and prevents blocking of the fluid passage. The indentation in the IOL and the channel or indentation in the S-IOL may also be applied in other embodiments of the assembly, like the embodiment shown in the other drawings.

As mentioned before, in FIGS. 40-46 an alternative embodiment of an IOL with an S-IOL is presented, showing in FIGS. 40 and 41 the IOL, in FIGS. 42 and 43 the IOL provided with the S-IOL, and FIGS. 44-46 the S-IOL.

Figure 40:
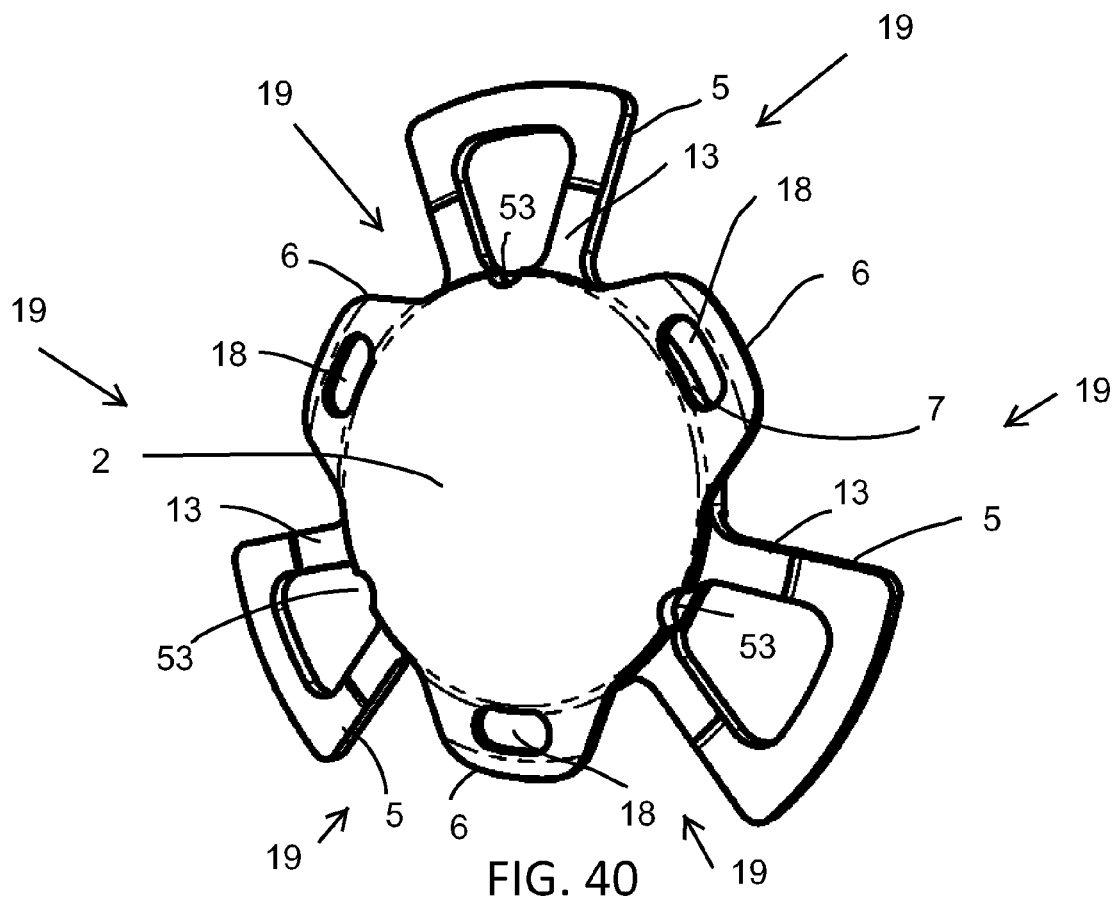
FIGS. 40-46 an alternative embodiment of an IOL with an S-IOL, showing in FIGS. 40 and 41 the alternative IOL, in FIGS. 42 and 43 the alternative IOL provided with the alternative S-IOL, and FIGS. 44-46 the alternative S-IOL.
Figure 41:
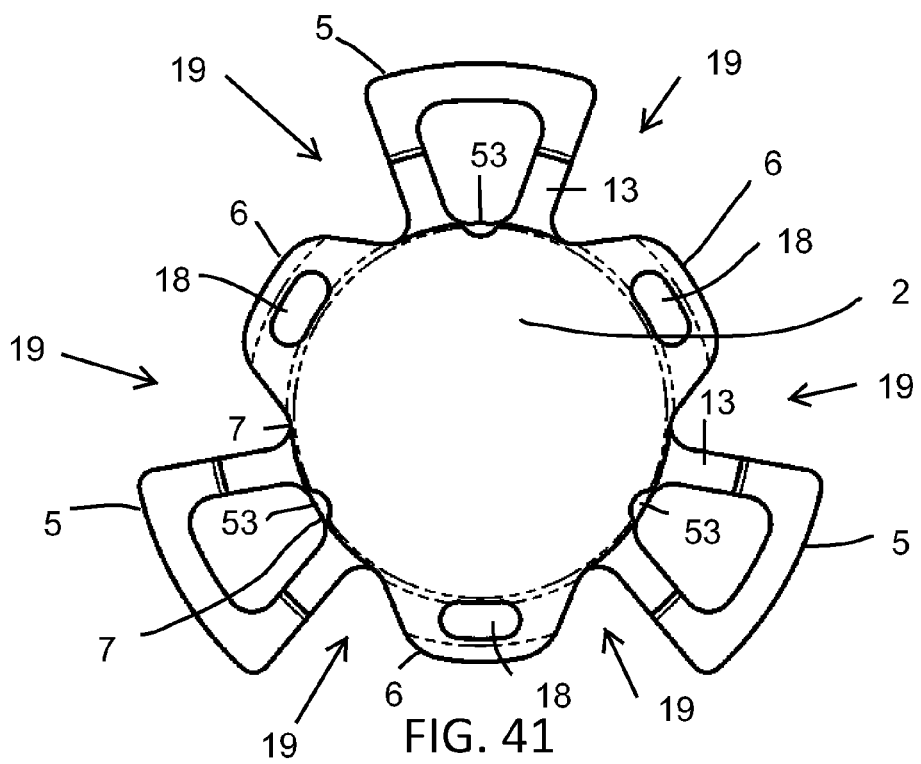

FIGS. 40 and 41 shown of another embodiment of an IOL allowing easier production, and easier implantation and fixation in an eye.

In this embodiment there are multiple posterior supports and multiple anterior supports. They are not separately indicated with an '-mark. The same parts or features again have the same references and will not be discussed further. FIG. 40 shows a perspective view and FIG. 41 shows a view from the anterior, showing the anterior side of the IOL.

There, the IOL has three haptics remaining in the (remainder of) the capsular bag. The haptics provide in fact six posterior supports 5 which are two by two coupled at their radial ends. They extend further in radial (Ra) direction then the anterior supports 6. When viewed like in FIG. 21, it is clear that the supports 5, 6 do not overlap. The through holed 18 in the anterior supports 6 again allows the anterior supports 6 to be brought out of the capsular bag easily. This can provide better centring in the capsular bag.

In the embodiment of FIGS. 40 and 41, the bottom 54 of the axial indentations 53 are further remote to the posterior direction then the anterior surfaces 13 of the posterior supports. This provides a more sure fluid channel. The axial indentations 53 in the perimeter 7 (also referred to as axial groove 53) may also taper in posterior direction. It was found that the indentations 53 resulted in an interruption of the posterior rim 16. As already explained, the posterior side of the IOL 1 at and near the perimeter is provided with a sharp rim 16 to prevent growth of tissue from the posterior capsular bag part. Such growth of tissue can cause posterior capsular opacification. The indentations 53 of the earlier embodiment interrupt that rim 16, thus presenting a risk of growth of tissue which may start posterior capsular opacification. This tissue may for instance block the indentation, preventing exchange of fluids.

Here, the indentation opens at the anterior side of the IOL. The depth (in axial direction A) is selected that the indentation extends past the edge 52 of the capsular bag once the IOL 1 is implanted. In practice, the indentation in axial direction A extends beyond the posterior surface 14, 14' of the anterior supports 6, 6'. In an embodiment, the indentation extends beyond the anterior surface 13, 13' of the posterior supports 5, 5'. Thus, the indentations provide a fluid channel past the capsular bag 23. The indentations 53 here end before the posterior rim 16, leaving its edge in tact. Thus, the indentations 53 have a bottom or end 54. The indentations 53 extend radially R inward with respect to the peripheral surface 7. The supports 5, 5', 6, 6' extend radially outward from the peripheral surface 7. Before implantation, in an embodiment, the posterior surface of the anterior supports 6, 6' in an embodiment in radial direction R extends past the peripheral surface 7. The anterior surface of the posterior supports 5, 5' in an embodiment in radial direction R extends past the peripheral surface 7 in opposite direction. Thus, the supports can clamp the capsular bag between them.

Again, the two-by-two connected posterior supports 5 may also provide the functionality of haptics. Another definition may be that there are three posterior supports that have through openings. The posterior supports 5 and anterior supports 6 again do not overlap. They are azimuthally shifted.

The posterior supports 5 may be angulated in anterior direction. Thus in some cases, fixation in the capsular bag may be improved. In the embodiment with angulation in anterior direction, the lens is pressed a little in posterior direction, and may rest against the posterior capsular bag part. When a through hole is also provided in the posterior capsular bag part, as explained earlier, fixation in that hole may improve.

Figure 42:
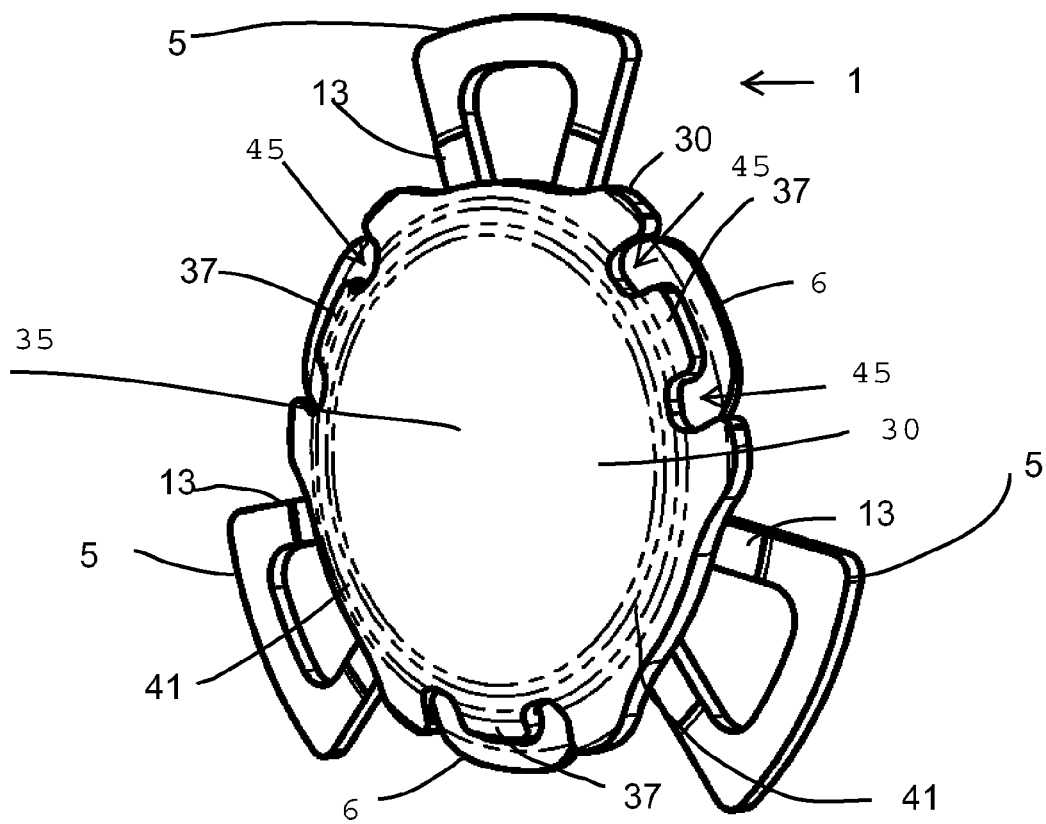
Figure 43:
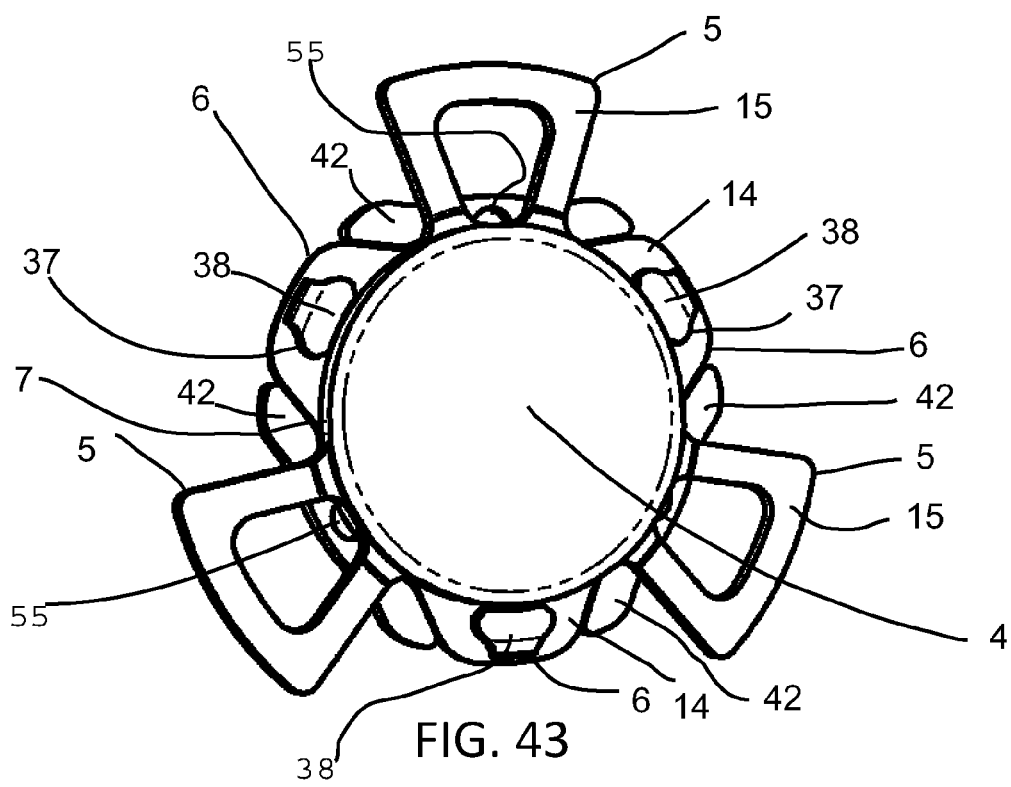

In FIGS. 42 and 43, the IOL of FIGS. 40/41 is shown with an S-IOL attached to it. In 42 the assembly is shown in perspective view from the anterior side, and in FIG. 43 from the posterior side.

The S-IOL 30 for the IOL 1 has in this embodiment three fixing parts 37, here all indicated as reference number 37. The S-IOL 30 again comprises a ring 41. The S-IOL 30 has an posterior ring surface 42 for resting against the anterior surface of the capular bag. The surface 42 is somewhat extended in radial direction to provide additional support. The fixing parts 37 comprise parts that extend through openings in the anterior supports 6. The S-IOL comprises holes 55 that communication with the indentations or axial grooves 53 described before. The holes 55 may be blind holes of even extend through the S-IOL (not indicated). This allows fluid communication.

Figure 44:
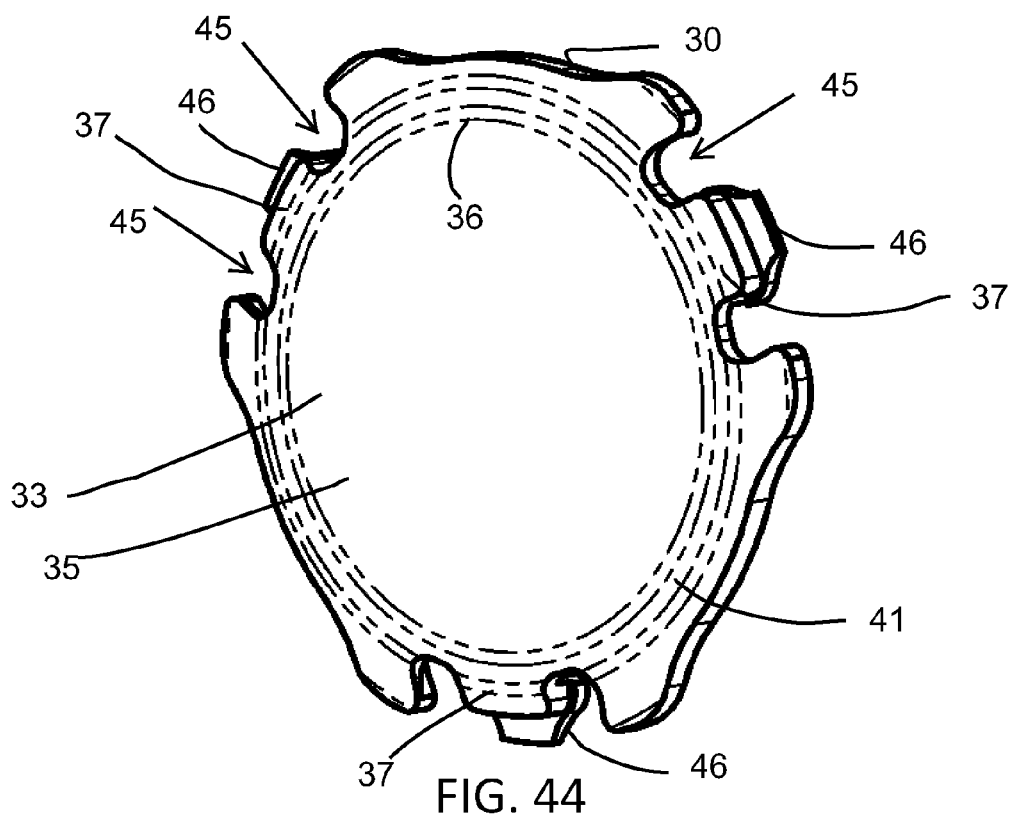
Figure 45:
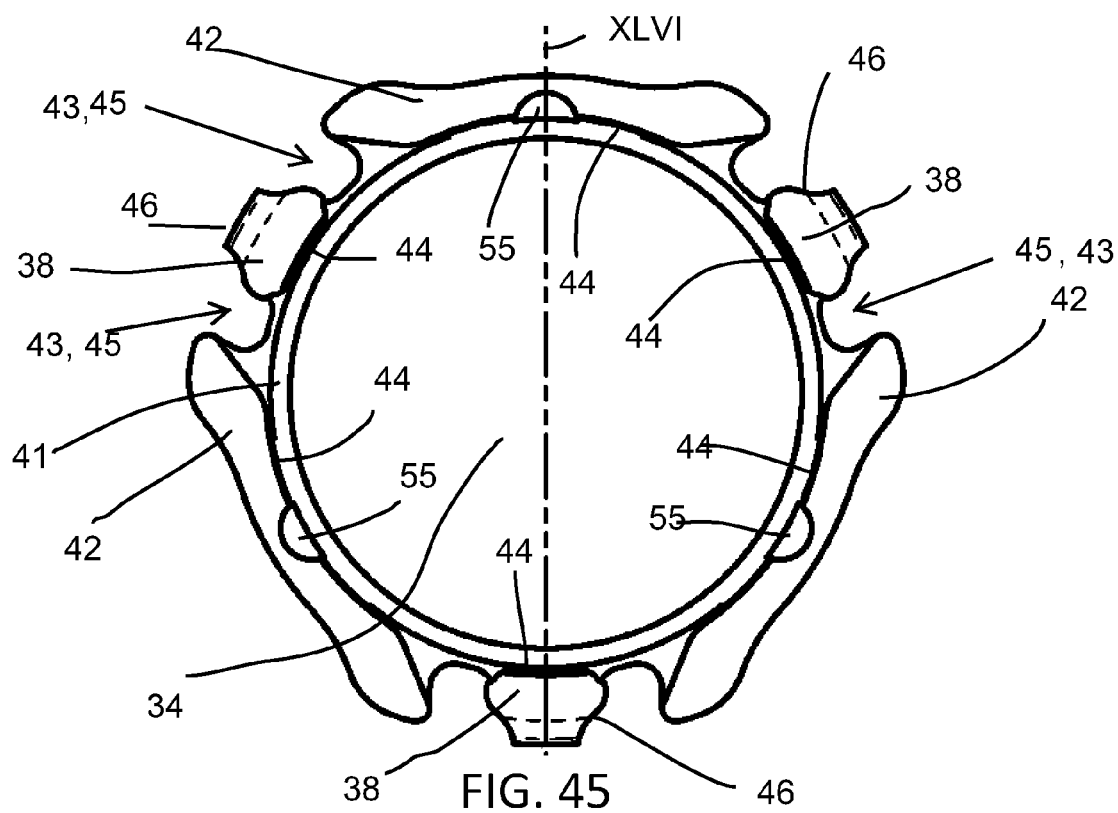
Figure 46:
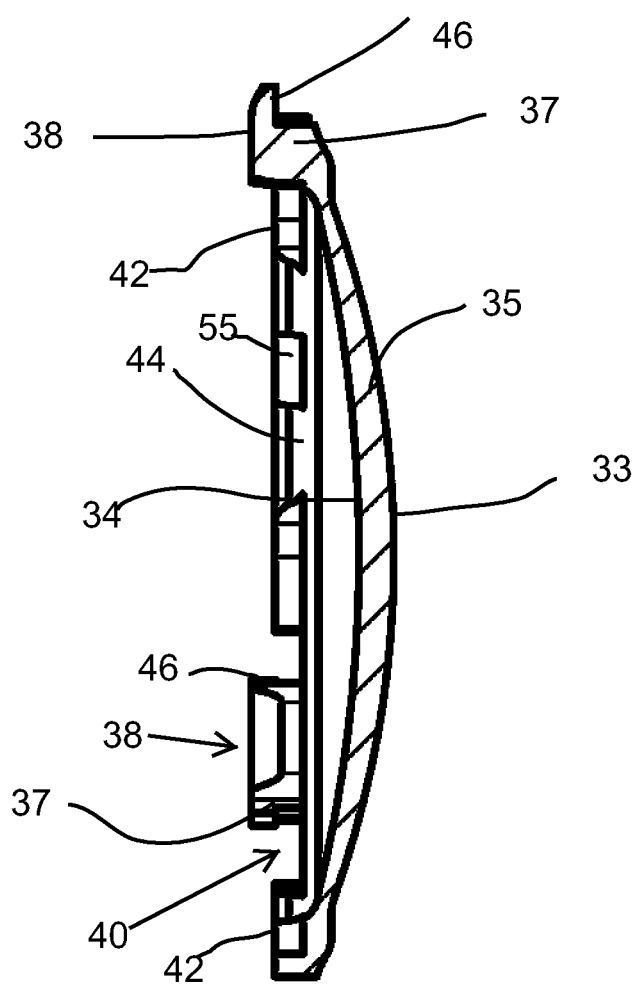

In FIGS. 44-46, the S-IOL 30 is shown in perspective view from in anterior side, in a top view from the posterior side, and a cross section as indicated in FIG. 45, respectively.

The fixing parts 37 comprises patches 46 that extend through holes in the anterior supports and that lock behind the anterior supports 6. The posterior surfaces 38 of the fixing parts 37 thus is able to rest against the anterior outer surface of the capsular bag. The posterior surfaces 38 may extend in axial posterior direction beyond the anterior surfaces 13 of the posterior supports 5. The S-IOL 30 here has cut-outs 45 that facilitate insertion of the fixing parts 37 on the anterior supports 6.

In all the embodiments and, in general in the IOL and S-IOL combination, one or both of the IOL and/or S-IOL may be provided with the optical zone or zones disclosed in PCT/NL2012/050115.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

LIST OF REFERENCE NUMBERS

1 Intra ocular lens structure (IOL)
2 Optical structure
3 Anterior surface of the IOL
4 Posterior surface of the IOL
5, 5' Posterior supports
6, 6' Anterior supports
7 perimeter of the IOL
8, 8' Additional anterior lips
9 Outer perimeter of the optical structure
10 Perimeter of the optical structure
11 Space between the posterior plane and anterior plane
12 Posterior groove for the posterior capsular bag flap
13, 13' (Anterior) Support surfaces of the posterior support
14, 14' (Posterior) Support surfaces of the anterior support
15 15' Posterior surfaces of the posterior support
16 Posterior rim
17, 17' Posterior surfaces of the additional anterior lips
18, 18' holes in the anterior support
19 azimuthal (Az) space between posterior and anterior supports
20 eyeball
21 Cornea
22 Capsular bag
23 Anterior part of the capsular bag
24 Posterior part of the capsular bag
25 Iris
26 pupil
30 secondary IOL (S-IOL)
31 natural lens
32 opening (in the anterior part of the capsular bag)
33 anterior surface of the S-IOL
34 posterior surface of the S-IOL
35 secondary optical structure/optical structure of the S-IOL
36 perimeter of the secondary optical structure
37, 37' fixing parts of the S-IOL
38, 38' posterior surface of the fixing parts of the S-IOL
39, 39' lips of the fixing parts for hooking the fixing parts onto anterior supports
40, 40' openings in said S-IOL between the perimeter of the secondary optical structure and the fixing parts
41 ring about the secondary optical structure
42 posterior ring surface formed for resting against the anterior capsular bag surface concentrically about the opening
43 cut-out in the ring for passing posterior and/or anterior support
44 inner ring surface of the ring, forming a peripheral/perimetrical ring surface about the perimeter of optical structure of the S-IOL
45 cut-out
46 patches
47 optical axis
48 fovea
49 pupillary axis
50 line of sight
51 visual axis
52 perimetrical edge of the capsular bag opening
53 indentation or axial groove
54 bottom of indentation or axial groove
55 hole in S-IOL communication with indentation
Ts Temporal side
Ns Nasal side
Az Azimutal direction
Ax Axial direction
Ra Radial direction

The invention claimed is:

1. An intra ocular lens assembly comprising an intra ocular lens structure (IOL) for placement in a capsular bag of an eye, said IOL comprising:
   an optical structure comprising an optical lens and a perimeter;
   at least two posterior supports, coupled to and radially extending from said perimeter of said optical structure, for residing inside the capsular bag when the IOL is implanted in the capsular bag, and
   at least two anterior supports, coupled to and radially extending from said perimeter of said optical structure, for residing outside the capsular bag when the IOL is implanted in the capsular bag, the anterior supports and the posterior supports mutually positioned on said perimeter for holding an anterior capsulotomy of the capsular bag between them for securing the optical structure of the IOL aligned with an opening defined by said anterior capsulotomy in an anterior wall of the capsular bag,
   at least two anterior lips, coupled to and radially extending from said perimeter of said optical structure, for residing outside the capsular bag when the IOL is implanted in the capsular bag,
   said intra ocular lens assembly further comprising a secondary intra ocular lens (S-IOL) for attachment on an anterior side of the IOL, said S-IOL comprising:
   a secondary optical structure comprising an optical lens and a secondary perimeter;
   at least two fixing parts, coupled with said secondary perimeter and each for coupling with one of said anterior lips, for fixing said S-IOL onto said IOL with the optical structure and the secondary optical structure aligned, and
   a ring about said secondary optical structure, with an inner perimeter of said ring attached to the secondary perimeter, said inner perimeter fitting about the perimeter of the optical structure of the IOL,
   wherein each of said posterior supports comprises an anterior capsular-engaging support surface designed and adapted for, when the IOL is implanted, engaging the posterior surface of the anterior wall of the capsular bag,
   wherein each of said anterior supports comprises a posterior capsular-engaging support surface designed and adapted for, when the IOL is implanted, engaging the anterior surface of the anterior wall of the capsular bag,
   wherein said posterior supports and said anterior supports of the IOL are in azimuthal sense (Az) shifted or staggered with respect to one another, wherein said S-IOL is designed and adapted, when the IOL is implanted, for implantation outside and anteriorly of the capsular bag.

2. The intra ocular lens assembly of claim 1, wherein said S-IOL comprises a posterior side facing the anterior side of said IOL, said anterior side of said IOL in use facing an iris of an eye, said ring comprises a posterior surface for engaging the anterior wall of the capsular bag, in particular said posterior surface axially positioned to at least be in plane with said posterior capsular-engaging support surfaces of the at least two anterior supports.

3. The intra ocular lens assembly of claim 1, wherein said at least two fixing parts are attached to said ring, in particular said fixing parts extending from a posterior surface of said ring.

4. The intra ocular lens assembly of claim 3, wherein said at least two fixing parts are attached to said ring and extend in posterior direction beyond the posterior surface of said ring, in particular said fixing parts extend in posterior direction beyond a posterior surface of the anterior lip it is coupled with.

5. The intra ocular lens assembly of claim 1, wherein said anterior supports comprise through holes or openings, and said fixing parts comprise ends provided with patches adapted for passing through said openings.

6. The intra ocular lens assembly of claim 1, wherein said inner perimeter of said ring comprises a inner peripheral surface which runs conical, and said perimeter of said optical structure of the IOL having a conical surface having substantially the same angle as the conical inner peripheral surface, said conical surfaces tapering in anterior direction.

7. The intra ocular lens assembly of claim 1, wherein
said at least two posterior supports comprise closed loops which extend from said optical structure, and each loop has both ends attached to said perimeter of said optical structure, and
said at least two anterior supports are each positioned within one of said loops between said ends.

8. The intra ocular lens assembly according to claim 1, wherein said posterior supports and said anterior supports of the IOL extend in azimuthal sense (Az) about the optical structure.

9. The intra ocular lens assembly according to claim 1, wherein an anterior side of said optical structure and a posterior side of said secondary optical structure facing said optical structure have substantially the same radius of curvature, in particular said anterior side of said optical structure and said posterior side of said secondary optical structure comprise a spacing.

* * * * *